United States Patent
Ito

(10) Patent No.: US 11,318,463 B2
(45) Date of Patent: May 3, 2022

(54) CELL TRANSFER APPARATUS AND CELL TRANSFER METHOD

(71) Applicant: YAMAHA HATSUDOKI KABUSHIKI KAISHA, Iwata (JP)

(72) Inventor: Saburo Ito, Shizuoka (JP)

(73) Assignee: YAMAHA HATSUDOKI KABUSHIKI KAISHA, Iwata (JP)

( * ) Notice: Subject to any disclaimer, the term of this patent is extended or adjusted under 35 U.S.C. 154(b) by 547 days.

(21) Appl. No.: 16/341,019

(22) PCT Filed: Oct. 17, 2016

(86) PCT No.: PCT/JP2016/080691
§ 371 (c)(1),
(2) Date: Apr. 10, 2019

(87) PCT Pub. No.: WO2018/073859
PCT Pub. Date: Apr. 26, 2018

(65) Prior Publication Data
US 2019/0224674 A1    Jul. 25, 2019

(51) Int. Cl.
*B01L 3/00* (2006.01)
*G06T 7/00* (2017.01)
(Continued)

(52) U.S. Cl.
CPC ......... *B01L 3/502715* (2013.01); *C12M 3/00* (2013.01); *C12M 23/12* (2013.01);
(Continued)

(58) Field of Classification Search
CPC ...... B01L 3/502715; B01L 2300/0829; C12M 3/00; C12M 23/12; C12M 33/04;
(Continued)

(56) References Cited

U.S. PATENT DOCUMENTS

2010/0197013 A1    8/2010   Kamp et al.
2012/0028288 A1*   2/2012   Nitta .................. G01N 33/5005
                                                        435/29
(Continued)

FOREIGN PATENT DOCUMENTS

CN       1241210 A     1/2000
JP    2006333710 A    12/2006
(Continued)

OTHER PUBLICATIONS

Michele Zanoni et al., "3D tumor spheroid models for in vitro therapeutic screening: a systematic approach to enhance the biological relevance of data obtained", Scientific Reports, vol. 6, No. 1, Jan. 11, 2016 (Jan. 11, 2016), pp. 1-11.
(Continued)

*Primary Examiner* — Michael L Hobbs
(74) *Attorney, Agent, or Firm* — Studebaker & Brackett PC

(57) ABSTRACT

A cell transfer apparatus transfers cells from a dish in which the cells are held to a microplate where a plurality of wells are classified into a plurality of groups. The cell transfer apparatus includes a camera unit that captures an image of the dish with the cells being held in the dish, an evaluation unit that gives evaluation levels to the plurality of cells held in the dish, respectively, based on the image of the dish with reference to predetermined multiple-step evaluation level for the cells, an allocation processor that sets transfer destinations of the cells on the dish so that the cells equal in evaluation level are distributed evenly to the groups in the microplate, and a shaft controller that transfers the cells in accordance with the transfer destinations set by the allocation processor.

17 Claims, 20 Drawing Sheets

(51) Int. Cl.
    *C12M 1/32*     (2006.01)
    *G06K 9/62*     (2022.01)
    *C12M 1/34*     (2006.01)
    *C12M 1/36*     (2006.01)
    *C12Q 1/02*     (2006.01)
    *C12M 3/00*     (2006.01)
    *C12M 1/26*     (2006.01)
    *G06V 10/40*     (2022.01)

(52) U.S. Cl.
    CPC ............ *C12M 33/04* (2013.01); *C12M 41/36* (2013.01); *C12M 41/48* (2013.01); *C12Q 1/02* (2013.01); *G06K 9/6267* (2013.01); *G06T 7/0014* (2013.01); *G06V 10/40* (2022.01); *B01L 2300/0829* (2013.01)

(58) Field of Classification Search
    CPC ......... C12M 41/36; C12M 41/48; C12Q 1/02; G06K 9/46; G06K 9/6267; G06T 7/0014
    See application file for complete search history.

(56) References Cited

U.S. PATENT DOCUMENTS

| | | |
|---|---|---|
| 2016/0304821 A1 | 10/2016 | Ito |
| 2017/0159002 A1 | 6/2017 | Ito |

FOREIGN PATENT DOCUMENTS

| | | |
|---|---|---|
| JP | 2011243188 A | 12/2011 |
| JP | 2015-062400 A | 4/2015 |
| JP | 2016163591 A | 9/2016 |
| WO | 2015087371 A1 | 6/2015 |
| WO | 2016/020989 A1 | 2/2016 |

OTHER PUBLICATIONS

Xue Gong et al., "Generation of Multicellular Tumor Spheroids with Microwell-Based Agarose Scaffolds for Drug Testing", PLOS ONE, vol. 10, No. 6, Jun. 19, 2015 (Jun. 19, 2015), pp. 1-18.

Jens M. Kelm et al., "Method for Generation of Homogeneous Multicellular Tumor Spheroids Applicable to a Wide Variety of Cell Types", Biotechnology and Bioengineering, vol. 83, No. 2, Jul. 20, 2003 (Jul. 20, 2003), pp. 173-180.

D. G. Buschke et al., "Noninvasive Sorting of Stem Cell Aggregates Based on Intrinsic Markers: Sorting of Intact Microtissues Based on NADH", NIH Public Access Author Manuscript, vol. 85, No. 4, Jan. 17, 2014 (Jan. 17, 2014), pp. 353-358.

Benedict Anchang et al., "CCAST: A Model-Based Gating Strategy to Isolate Homogeneous Subpopulations in a Heterogeneous Population of Single Cells", PLOS Computational Biology, vol. 10, No. 7, Jul. 31, 2014 (Jul. 31, 2014), pp. 1-14.

Extended European Search Report issued by the European Patent Office dated Sep. 24, 2019, which corresponds to EP16919403.2-1132 and is related to U.S. Appl. No. 16/341,019.

Saburo Ito, et al., "Primary Organoid o Mochiita High-throughput Screening to Organoid Jido Bunpai Sochi", Dai 23 Kai Human & Animal Bridging Research Organization Gakujutsu Nenkai, Jun. 20, 2016, p. 95, p. 24.

Kiyohara Y. et al., "Drug screening and grouping by sensitivity with a panel of primary cultured cancer spheroids derived from endometrial cancer", Cancer Science, Apr. 2016, vol. 107, No. 4, p. 452-460.

International Search Report issued in PCT/JP2016/080691; dated Jan. 10, 2017.

An Office Action mailed by China National Intellectual Property Administration dated Oct. 11, 2021, which corresponds to Chinese Patent Application No. 201680090064.2 and is related to U.S. Appl. No. 16/341,019; with English language summary.

* cited by examiner

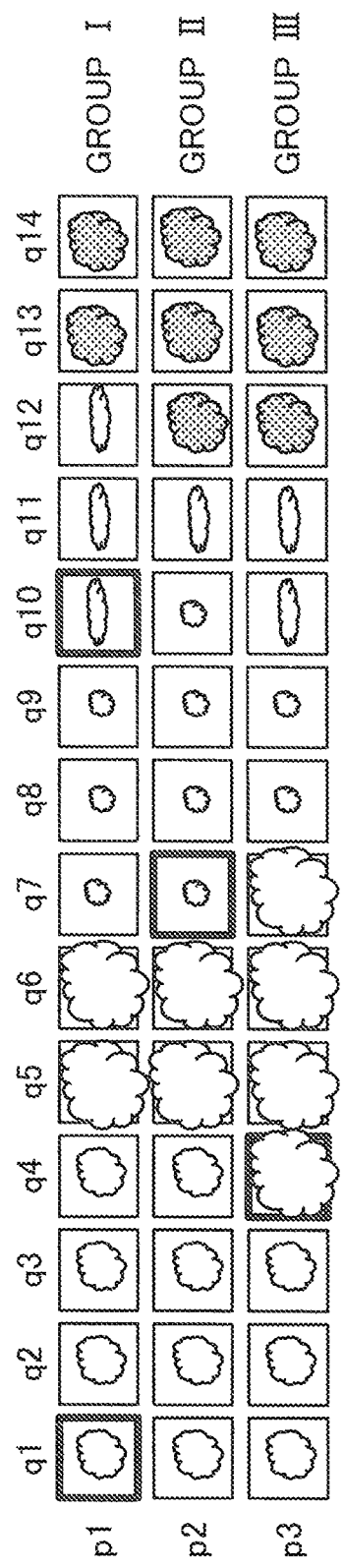

FIG.17

|    | q1 | q2 | q3 | q4 | q5 | q6 | q7 | q8 |           |
|----|----|----|----|----|----|----|----|----|-----------|
| p1 | G1 | G1 | G2 | G2 | G3 | G3 | G4 | G4 | GROUP I   |
| p2 | G1 | G1 | G2 | G2 | G3 | G3 | G4 | G4 | GROUP II  |
| p3 | G1 | G1 | G2 | G2 | G3 | G3 | G4 | G4 | GROUP III |

CELL TRANSFER APPARATUS AND CELL TRANSFER METHOD

CROSS-REFERENCE TO RELATED APPLICATION

This application is a National Stage of International Patent Application No. PCT/JP2016/080691, filed Oct. 17, 2016, the entire content of which is incorporated herein by reference.

BACKGROUND

Technical Field

The present disclosure relates to a cell transfer apparatus and a cell transfer method for transferring cells from a dish in which the cells are held to a plate having a well for receiving the cells.

Background Art

For example, in a use for medical and biological studies, a single cell, a cell aggregate obtained by three-dimensionally clumping cells, or a cell clump obtained by clumping cellular fragments and culturing the clump (hereinafter, they are simply referred to herein as cells) are accommodated in wells arranged in a matrix pattern on a microplate in some cases to be subject to processing such as observation, checking for medicinal effect, inspection, or culture. The cells to be accommodated in the wells are sorted on the dish having recessed portions capable of accommodating the cells. Prior to the sorting, a cell culture solution containing a lot of cells is dispersed on the dish, and the cells are held in the recessed portions. Thereafter, images of the dish in which the cells are held are captured, and the cells are classified into usable cells, and unusable cells and foreign substances by an image processing technique. After a while, the usable cells are sucked from the recessed portions by a suction tip, and the sucked cells are discharged onto the wells of the microplate as described, for example, in WO2015/087371A1.

The plurality of wells of the microplate are classified into specified purpose groups in some cases. For example, a cell culture solution containing a first compound is poured in a well family in a first group, and a cell culture solution containing a second compound is poured in a well family in a second group. Then, an observation is made as to how the first and second compounds to affect the cells. In this case, it is desirable, for equal evaluation of sensitivities to the first and second compounds, that cells with equivalent quality are distributed evenly to each of the first and second groups. However, the cells determined to be usable on the dish vary in size, shape, and property. For this reason, in a method for simply assigning numbers to cells on the dish and causing a suction tip to sequentially suck the cells to be moved to the wells, it is difficult to evenly distribute the cells with equivalent quality to a plurality of groups.

SUMMARY

Accordingly, the present disclosure provides a cell transfer apparatus and a cell transfer method that transfer cells from a dish holding the cells to a microplate having the wells for receiving the cells enable the cells with equivalent quality to be distributed evenly to wells in a plurality of groups.

One aspect of the present disclosure provides a cell transfer apparatus including a dish having a plurality of holding portions holding a plurality of cells to be transferred, and a microplate having a plurality of wells that receive the cells, with the plurality of wells being classified into a plurality of groups. The cell transfer apparatus further includes a transfer unit that transfers the cells from the dish to the microplate, an imaging unit that captures an image of the dish with the cells being held by the plurality of holding portions, an evaluation unit that gives evaluation levels to the cells held in the dish, respectively, based on the image of the dish, an allocation processor that sets transfer destinations of the cells on the dish so that the cells equal in evaluation level are distributed evenly to each of the plurality of groups in the microplate, and a transfer controller that causes the transfer unit to transfer the cells held by the holding portions of the dish to the plurality of wells in the plurality of groups in the microplate, respectively, based on the transfer destinations set by the allocation processor.

Another aspect of the present disclosure provides a cell transfer method for transferring a cell held in a dish to a microplate where a plurality of wells are classified into a plurality of groups. The cell transfer method includes capturing an image of the dish in which the cell to be transferred is held, giving evaluation levels to the plurality of the cells held in the dish, respectively, based on the image of the dish with reference to predetermined multiple-step evaluation levels for the cells, setting transfer destinations of the plurality of the cells on the dish so that the cells equal in evaluation level are distributed evenly to each of the plurality of groups in the microplate, and transferring the plurality of the cells held in the dish to the plurality of wells in the plurality of groups in the microplate, respectively, based on the setting of the transfer destinations.

These objects, features, and advantages of the present disclosure will become more apparent from the following detailed description taken in conjunction with the accompanying drawings.

BRIEF DESCRIPTION OF THE DRAWINGS

FIG. 14 is a diagram for describing a second modified example of the present embodiment;

FIG. 17 is a pattern diagram illustrating an example of even allocation of the cells into the microplate;

DETAILED DESCRIPTION

Embodiments of the present disclosure will be described in detail below with reference to the drawings. Subjects to be transferred in the present disclosure are cells derived from a biological object, particularly, a cell aggregate (spheroid) or a cell clump obtained by clumping cellular fragments and culturing the clump. The cell aggregate derived from a biological object is produced by clumping several cells to hundreds of thousands of cells. For this reason, the cell aggregate varies in size. The cell aggregate produced by living cells has an approximately spherical shape. However, the alternation or death of some cells producing the cell aggregate makes the cell aggregate irregular in shape and density in some cases. In tests for biotechnology and medical technology, a cell transfer apparatus picks up usable cell aggregates from a plurality of cell aggregates having various shapes supported by a dish on a sorting stage and transfers the picked-up cell aggregates to a microplate. In the microplate, the cell aggregates undergo various processes including observation, checking for medicinal effect, inspection, and culture. In the following description, the above-described cell aggregates are simply expressed as cells C.

[Entire Configuration of Cell Transfer Apparatus]

Figure 1:
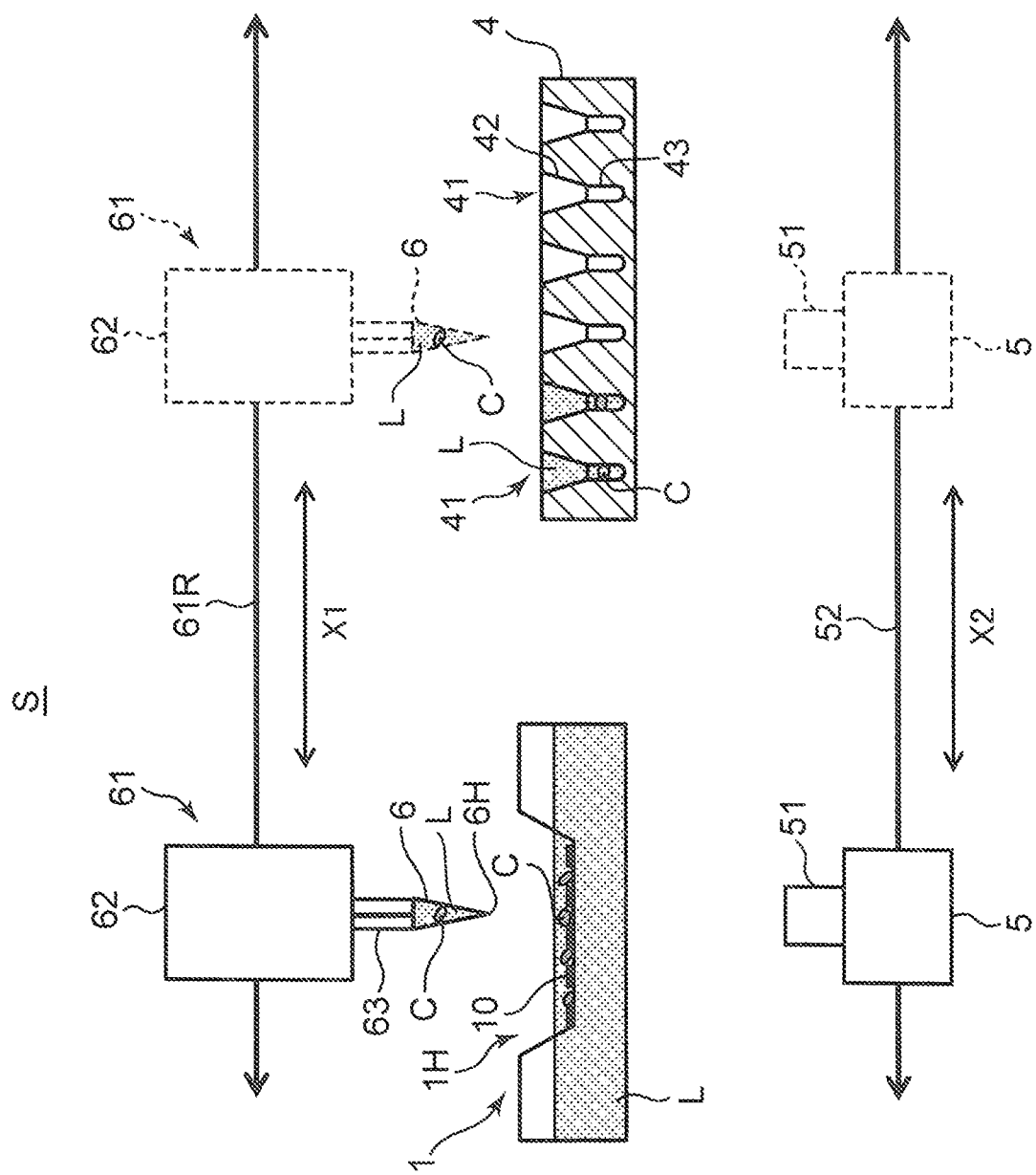
FIG. 1 is a schematic diagram illustrating a configuration of a cell transfer apparatus according to an embodiment of the present disclosure.

FIG. 1 is a diagram schematically illustrating an entire configuration of a cell transfer apparatus S. Herein, the diagram illustrates the cell transfer apparatus S that transfers the cells C between two containers. The cell transfer apparatus S includes a sorting container 1 having a dish 10, a microplate 4, a camera unit 5 (an imaging unit), and a head unit 61 (a transfer unit) mounted with a tip 6.

The sorting container 1 is a container that is a transfer source of the cells C stores a culture medium L, and holds the dish 10 for cell sorting with the dish 10 being immersed in the culture medium L. The dish 10 is a plate that supports the cells C and has a plurality of holding recessed portions 3 on an upper surface of the dish 10. The holding recessed portions 3 can accommodate the cells C separately.

The culture medium L is not particularly limited as long as it prevents deterioration in properties of the cells C, and thus any culture medium can be selected appropriately based on types of the cells C. Examples of the culture medium L include a base medium, a synthetic medium, an Eagle medium, a Roswell Park Memorial Institute (RPMI) medium, a Fischer's medium, a Ham's medium, a Molecular, Cellular, and Developmental Biology (MCDB) medium, and a serum medium, as well as cell freezing liquids such as glycerol and a cell banker (manufactured by Juji Field Inc.) to be added before cryopreservation, formalin, a reagent for fluorescent stain, an antibody, purified water, and normal saline. For example, in the case where BxPC-3 (human pancreatic adenocarcinoma cells), which is a cell derived from a biological object is used as the cell C, the culture medium L to be used is created by blending 10% of a fetal bovine serum (FBS) in a RPMI-1640 medium and adding antibiotic and a supplement such as sodium pyruvate if necessary.

The sorting container 1 has a cylindrical shape and includes an upper opening 1H having an orthogonal shape on an upper surface of the sorting container 1. The upper opening 1H is used for putting the cells C into the sorting container 1 and picking up sorted cells C. The dish 10 is disposed below the upper opening 1H. The sorting container 1 and the dish 10 to be used are made of transparent resin material or glass. This material enables the cells C supported by the dish 10 to be observed through the camera unit 5 disposed below the sorting container 1.

A plurality of cells C that has been dispersed in a cell culture solution are put into the sorting container 1 through a dispensing tip, unillustrated. The dispensing tip sucks the cell culture solution along with the cells C from the container that stores the cell culture solution containing a lot of the cells C, and internally holds the sucked cell culture solution. Thereafter, the dispensing tip is moved above the sorting container 1, and accesses to the upper surface of the dish 10 through the upper opening 1H. Then, the cells C held inside the tip are discharged along with the cell culture solution with a front end opening of the dispensing tip being immersed in the culture medium L of the sorting container 1.

The microplate 4 is a container that is a transfer destination of the cells C, and includes a plurality of wells 41 that receive the cells C. One of the wells 41 accommodates a necessary number (normally one) of the cells C along with the culture medium L. The microplate 4 to be used is also made of transparent resin material or glass. This material enables the cells C supported by the microplate 4 to be observed through the camera unit 5 disposed below the microplate 4.

The camera unit 5 includes a camera lens 51, and captures an image of the cells C supported by the dish 10 in the sorting container 1 or an image of the cells C held in the wells 41 in the microplate 4. The camera unit 5 includes an image pickup device such as a charged-coupled device (CCD) image sensor. The camera lens 51 causes an optical image of the cells C to be formed on a light receiving surface of the image pickup device.

The camera unit 5 is disposed below the sorting container 1 and the microplate 4 so that the camera lens 51 faces lower surfaces of the sorting container 1 and the microplate 4. That is, the camera unit 5 captures an image of the cells C supported by the sorting container 1 or the microplate 4 from a lower surface side of the sorting container 1 or the microplate 4. The camera unit 5 can, as indicated by arrow X2 in the figure, travel between a position below the sorting container 1 and a position below the microplate 4 horizontally along a guide rail 52.

The tip 6 is a tubular member having a front end opening 6H, and sucks and discharges the culture medium L containing the cells C. Specifically, the tip 6 sucks the cells C from the dish 10 of the sorting container 1, more specifically, the cells C supported by the holding recessed portion 3 on the dish 10 along with the culture medium L, and discharges the sucked cells C to the wells 41 of the microplate 4. Further, although unillustrated, the tip 6 sucks a reagent liquid and the like if necessary, and discharges the reagent liquid to the inside of the wells 41 that supports the cells C.

The head unit 61 is disposed to transfer the cells C from the dish 10 to the microplate 4, and includes a head main body 62 and a head 63. The head main body 62 holds the head 63 so that the head 63 is capable of reciprocating in an up and down direction. The head main body 62 can travel in a right and left direction along a guide rail 61R as indicated by arrow X1 in the figure. Note that, although unillustrated in FIG. 1, the head main body 62 can travel also in a direction perpendicular to a sheet surface of FIG. 1 (a front-rear direction). The head 63 is a hollow rod. The tip 6 is mounted on a lower end of the head 63. A piston mechanism is mounted into the hollow portion of the head 63, and an operation of the piston mechanism applies a suction force and a discharge force to the front end opening 6H of the tip 6. The head main body 62 includes a power unit of the piston mechanism, an ascending and descending mechanism that moves the head 63 in the up and down direction, and a power unit of the ascending and descending mechanism.

[Details of Dish and Microplate]

Figure 2:
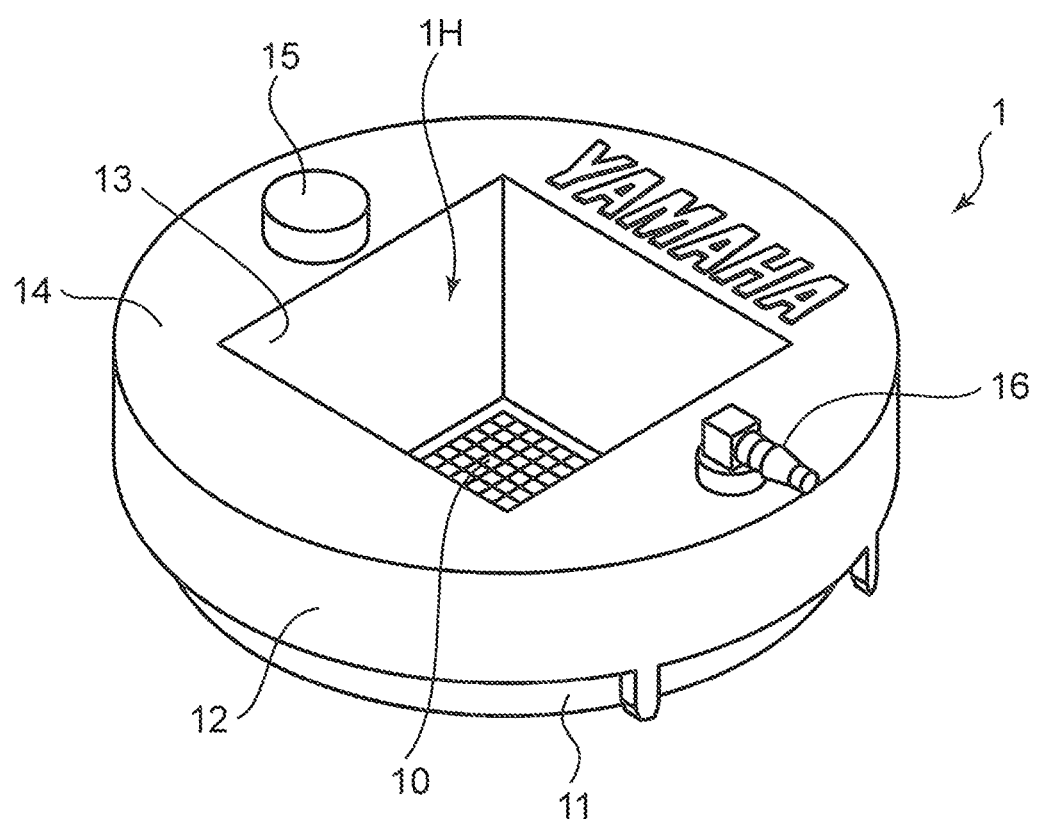
FIG. 2 is a perspective view illustrating a sorting container to be used in the cell transfer apparatus.
Figure 3:
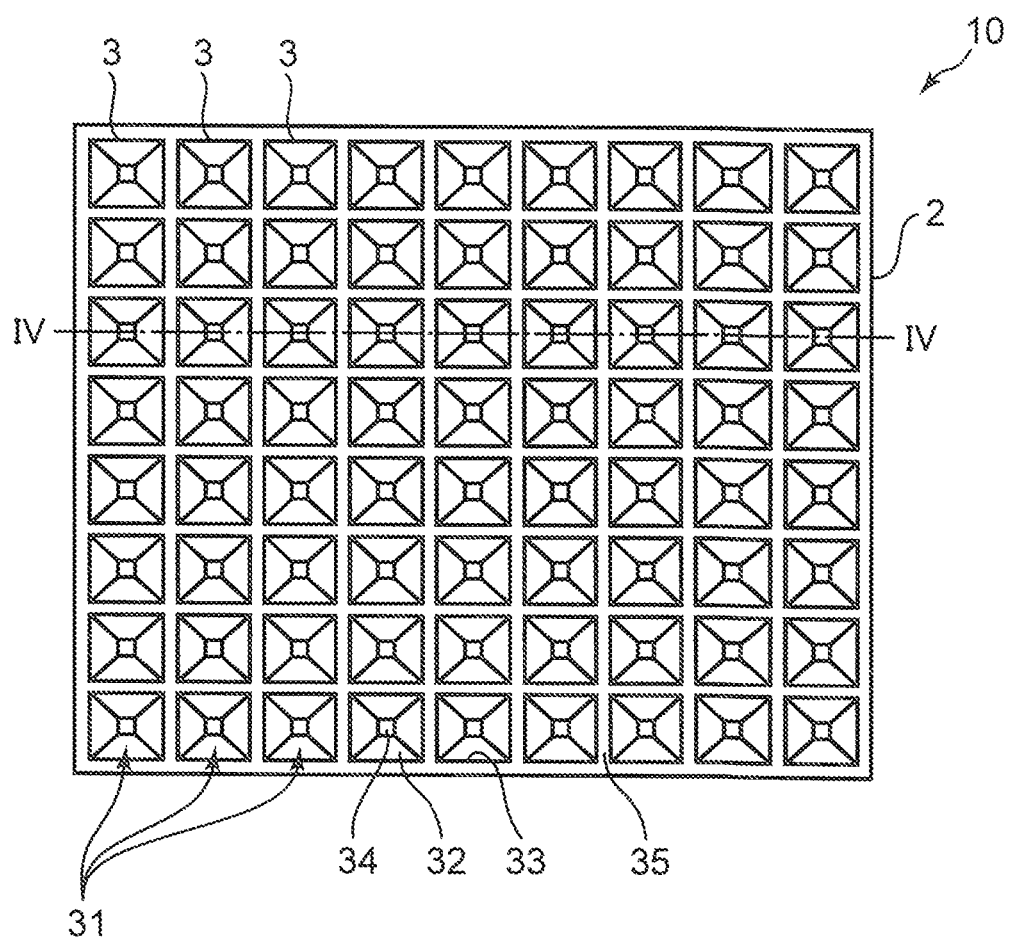
FIG. 3 is a top view illustrating a dish of the sorting container.
Figure 4:
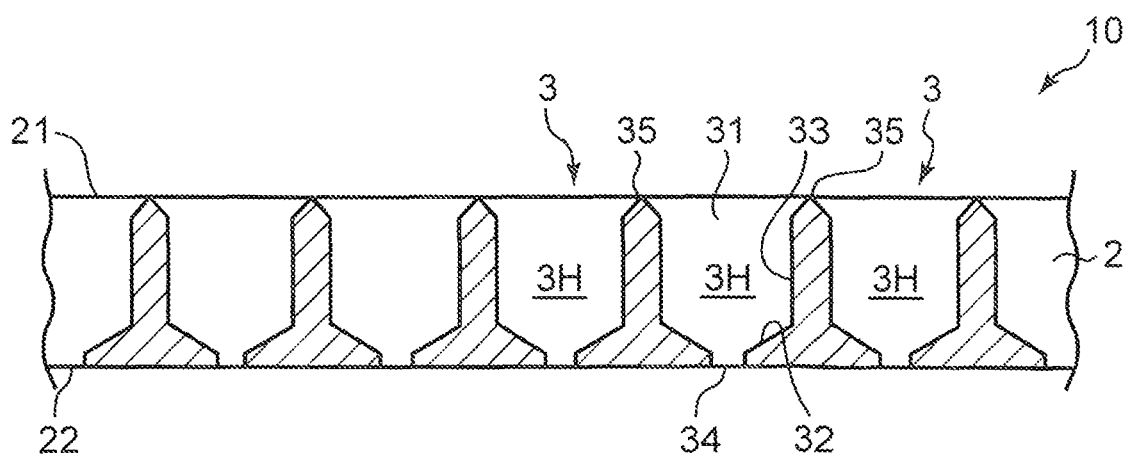
FIG. 4 is a cross-sectional view taken along line IV-IV in FIG. 3.

FIG. 2 is a perspective view of the sorting container 1. FIG. 3 is a top view of the dish 10. FIG. 4 is a cross-sectional view taken along line IV-IV in FIG. 3. The sorting container 1 includes a bottom plate 11, an external wall 12, an internal wall 13, and a ceiling wall 14. The bottom plate 11 is a cylindrical plate member that constitutes a bottom portion of the sorting container 1. The bottom plate 11 has an opening on its top surface. The external wall 12, the internal wall 13, and the ceiling wall 14 constitute a lid member that covers the bottom plate 11. The external wall 12 is a portion that is larger in diameter than a side peripheral wall of the bottom plate 11, and the internal wall 13 is a square tubular portion disposed inside the external wall 12. The ceiling wall 14 is a board member that covers a region other than the upper opening 1H on the upper surface side of the sorting container 1.

The internal wall 13 defines the upper opening 1H, and tilts downward from the upper opening 1H so that an opening area gradually decreases. The ceiling wall 14 is perforated with a work hole 15 formed by a vertical through hole. The culture medium L, a chemical or the like is poured into a cavity of the sorting container 1 through the work hole 15, or the culture medium L is sucked or discharged through the work hole 15. Further, a piping connection port 16 for adjusting air pressure in the cavity of the sorting container 1 is disposed on the ceiling wall 14.

The dish 10 includes a dish main body 2 and a plurality of holding recessed portions 3 (holding portions) formed in the dish main body 2. The dish main body 2 includes a board-shaped member having a predetermined thickness, and has an upper surface 21 and a lower surface 22. The plurality of holding recessed portions 3 that holds the cells C to be transferred are disposed on the upper surface 21. The dish 10 is held at a lower end portion of the internal wall 13 with a space being left between the lower surface 22 and the bottom plate 11 of the sorting container 1. The dish 10 is immersed in the culture medium L in the sorting container 1. That is, the culture medium L is poured into the sorting container 1 so that the upper surface 21 of the dish 10 is located below a liquid surface of the culture medium L.

Each of the holding recessed portions 3 includes an opening 31, a bottom portion 32, a tubular wall surface 33, a hole portion 34, and a boundary portion 35. The present embodiment describes an example where the holding recessed portions 3 having a square shape when viewed from the top are arranged in a matrix pattern. The opening 31 is a square opening disposed on the upper surface 21, and has a size sufficient to allow the front end opening 6H of the tip 6 for sorting to pass therethrough. The bottom portion 32 is disposed near the lower surface 22 inside the dish main body 2. The bottom portion 32 is a tilted surface that gently tilts down toward the center (the center of the square). The tubular wall surface 33 is a wall surface that extends vertically downward to the bottom portion 32 from the opening 31. The hole portion 34 is a through hole that vertically pierces between the center of the bottom portion 32 and the lower surface 22. The hole portion 34 has a square shape when viewed from the top, and is concentric with the opening 31. The boundary portion 35 that is disposed on the upper surface 21 is a ridge line that forms an opening edge of each of the holding recessed portions 3 and separates the holding recessed portions 3 from each other. Note that each of the holding recessed portions 3 may have a circular, triangular, pentagonal, or hexagonal shape when viewed from the top, and they may be disposed in the dish main body 2 into a honeycomb, linear, or random pattern. Alternatively, the dish 10 may have only one holding recessed portion 3.

The bottom portions 32 and the tubular wall surfaces 33 of the holding recessed portions 3 define the dish 10 into accommodation spaces 3H that accommodates the cells C. Generally, each of the accommodation spaces 3H is designed to accommodate one cell C. Therefore, each of the holding recessed portions 3 is set based on a size of a target cell C. In dispersion of a cell culture solution containing a lot of the cells C into the sorting container 1, however, the plurality of cells C enter one holding recessed portion 3 in some cases. The hole portions 34 are disposed to release small cells other than cells with desired size and foreign substances through the accommodation spaces 3H. Therefore, the hole portions 34 each has a size such that the cells C with desired size fail to pass but small cells other than the cells C with desired size or foreign substances pass through the hole portions 34. As a result, the cells C to be sorted are trapped in the holding recessed portions 3, whereas foreign substances or the like drop from the hole portion 34 onto the bottom plate 11 of the sorting container 1.

Figure 5:
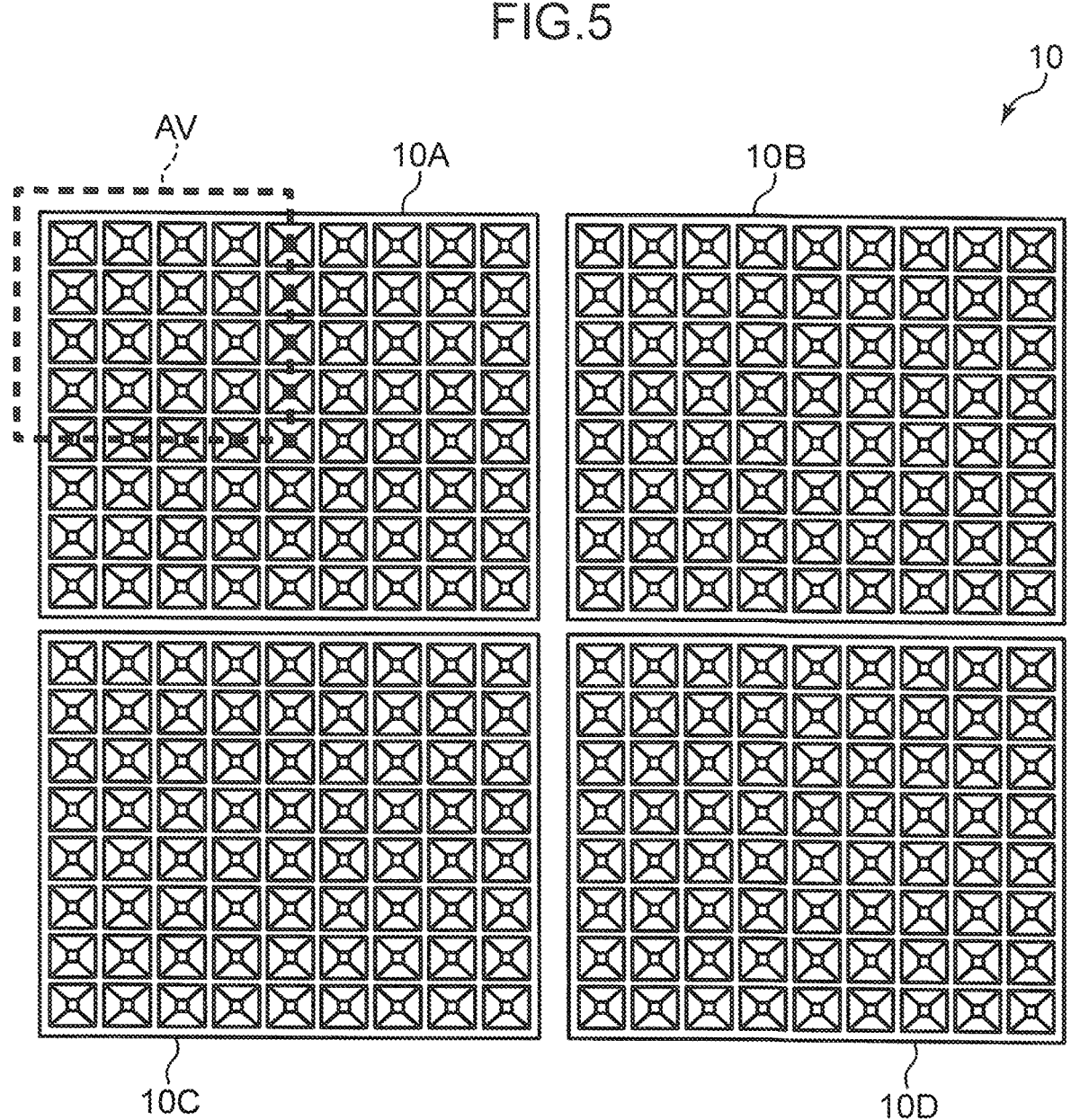
FIG. 5 is a top view illustrating a plurality of dishes and an image capturing range.

FIG. 5 is a diagram illustrating an actual arrangement example of the dish 10 in the sorting container 1. Herein, the illustrated example is the dish 10 that is constituted by disposing four small rectangular dishes 10A, 10B, 10C, and 10D to form one large rectangle. The holding recessed portions 3 that hold the cells C of micron order on the dish 10 have a minute size, and thus a thin plate is naturally used in the dish main body 2. In this case, since enlargement of the plate size deteriorates flatness of the plate, the dish 10 is frequently formed into a desired size by collecting the small dishes 10A to 10D with small size. Much the same is true on the microplate 4.

FIG. 5 also illustrates one example of an image capturing range AV, on the dish 10, of the camera unit 5. An angle of view of an optical system that captures images of the cells C of micron order decreases naturally. In general, a camera with the angle of view being about 2 mm is used. Therefore, one image capturing operation to be performed by the camera unit 5 fails to entirely cover the dish 10. For this reason, in a method to be used herein, the camera unit 5 sequentially captures images of separated areas of the dish 10. FIG. 5 illustrates the image capturing range AV that covers about ¼ of the small dish 10A, but actually several dozens to one hundred image capturing operations are required to cover only the entire area of the one small dish 10A. Therefore, in the example of FIG. 5, the use of the four small dishes 10A to 10D requires four times image capturing operations.

Figure 6:
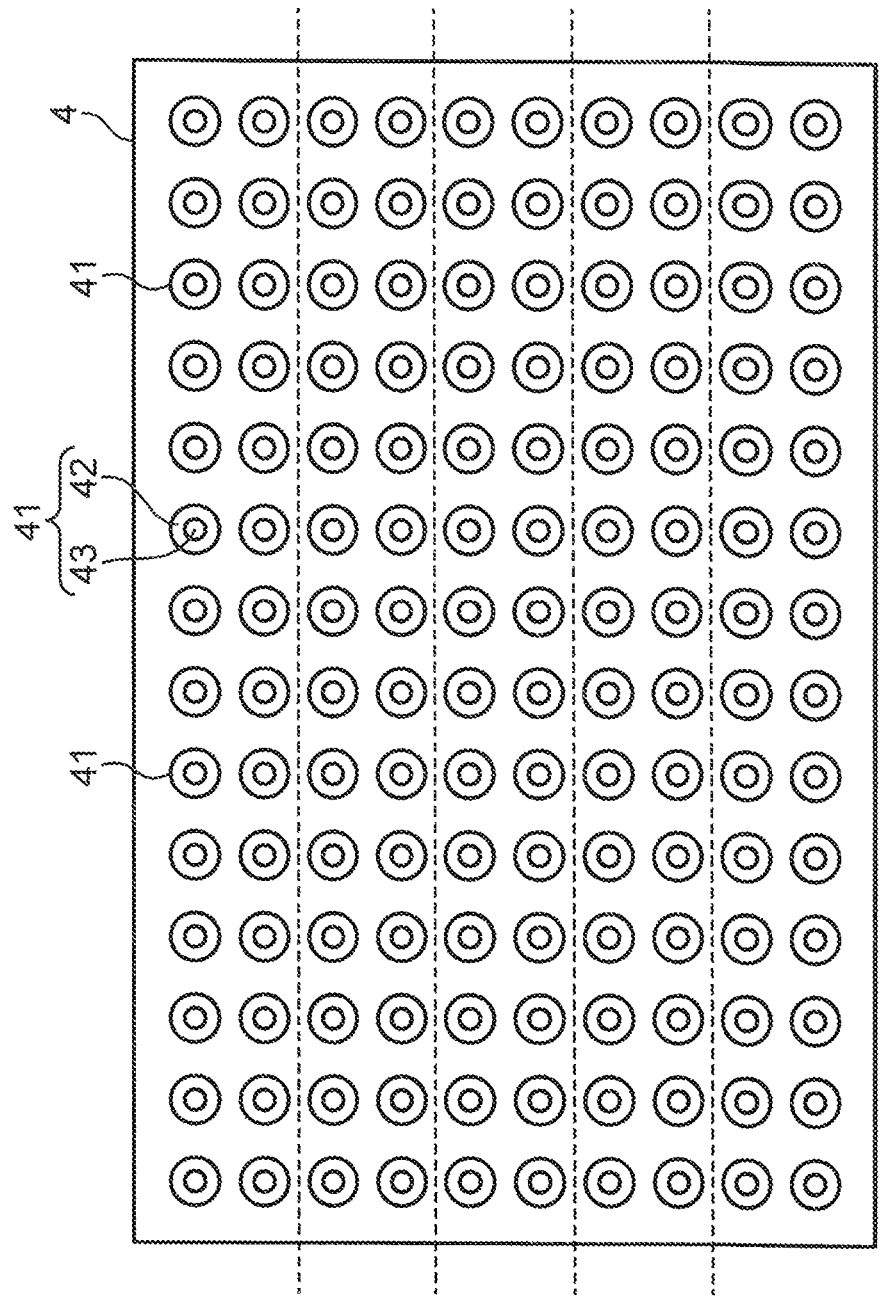
FIG. 6 is a top view illustrating a microplate to be used in the cell transfer apparatus.

FIG. 6 is a top view illustrating the microplate 4. The microplate 4 is constituted by arranging, in a matrix pattern, a lot of wells 41 with opened top surfaces. As illustrated in FIG. 1, the wells 41 each includes a tapered portion 42 and a tubular portion 43 connected with a lower part of the tapered portion 42. The tapered portion 42 has a circular opening on an upper surface of the microplate 4, and has a tapered shape such that a diameter gradually decreases downward from the upper surface. The tubular portion 43 has an inner diameter that is uniform in the up and down direction, and includes a bottom portion on its lower end. Similarly to the example of the dish 10 illustrated in FIG. 5, the plurality of small microplates may, for example, be integrated in a frame member to form one microplate 4.

A standard plate of 85.48 mm×127.76 mm is used as the microplate 4 (see "Footprint Dimensions—for Microplates" defined by Society for Laboratory Automation and Screening (SLAS) of American National Standards Institute (ANSI) in 2004). In this case, a general number of the wells 41 is 24 pieces×16 pieces, and the wells 41 are arranged in a matrix pattern with a predetermined pitch. FIG. 6 illustrates an example where 14 pieces×10 pieces of the wells 41 are arranged in a matrix pattern.

Figure 7:
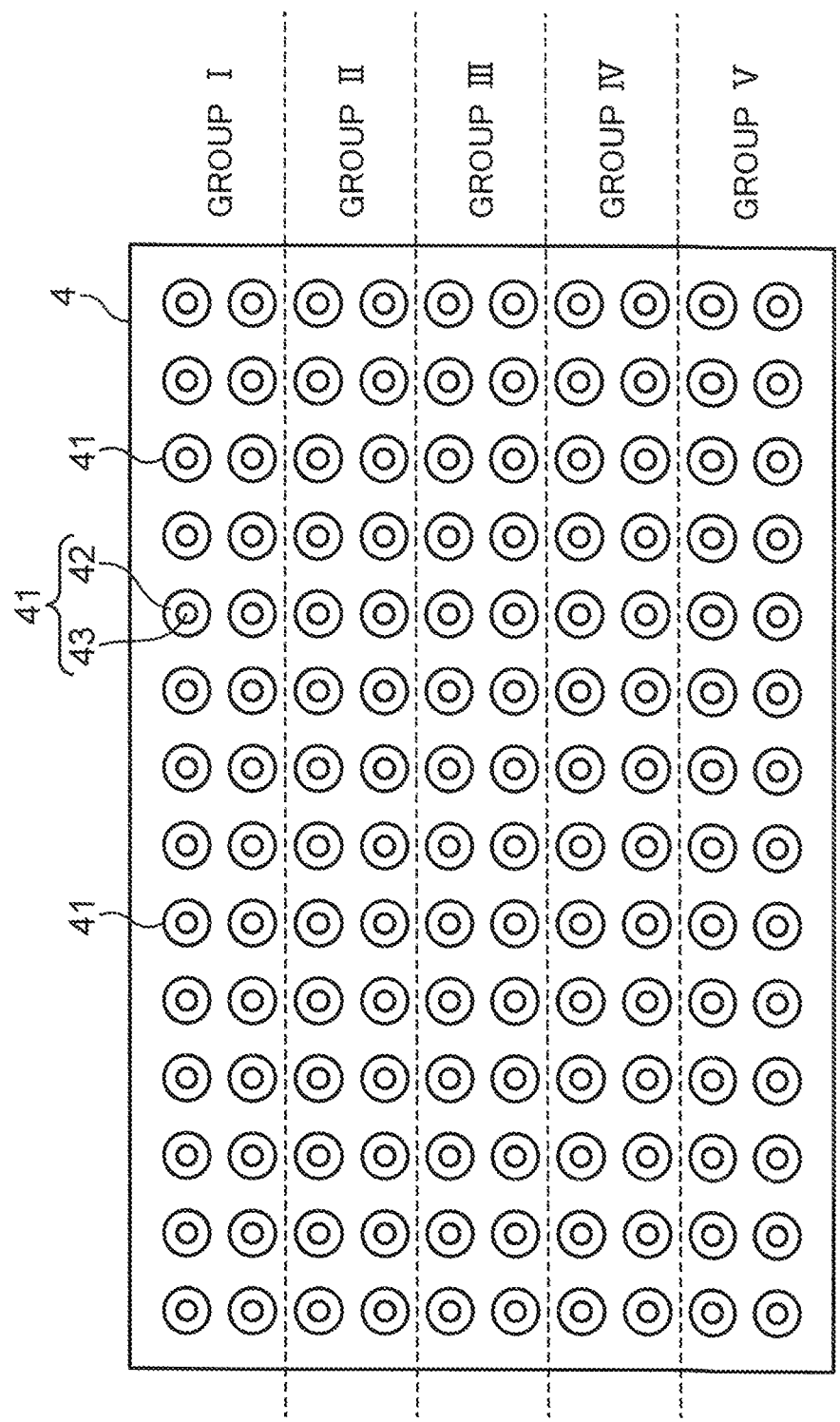
FIG. 7 is a top view illustrating an example where a lot of wells of the microplate are classified into a plurality of groups.

In the present embodiment, the plurality of wells 41 of the microplate 4 to be used are classified into groups having specific purposes. FIG. 7 illustrates an example where the wells 41 of the microplate 4 are classified into five groups I, II, III, IV, and V. The groups I to V each has the wells 41 of 2 rows×14 columns Herein, different cell culture solutions are poured in well 41 families in the groups. For example, a cell culture solution containing a first compound is poured in a well 41 family in the group I, and a cell culture solution containing a second compound is poured in a well 41 family in the group II, and so on. Then, an observation is made as to how the first, second and the other compounds to affect the cells C. Naturally, the group classification in FIG. 7 is an example, and thus the mode of the group classification for the wells 41 is set as desired in accordance with a purpose. In the present disclosure, "the wells are classified into the plurality of groups" means that, as described above, the wells 41 are classified visually on the microplate 4 and the wells 41 are virtually classified in a controller 7 (FIG. 9), described later.

Figure 8:
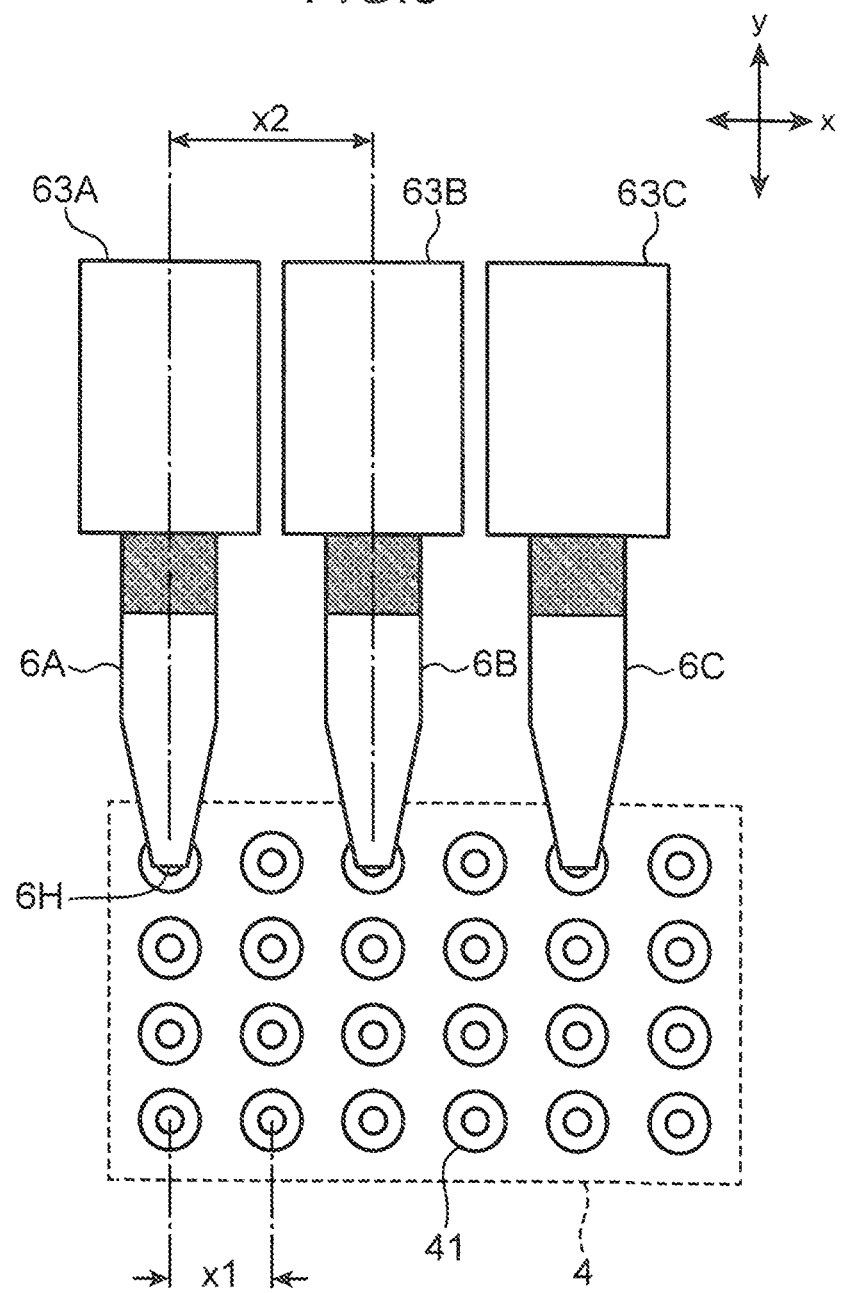
FIG. 8 is a diagram for describing an example where a plurality of tips simultaneously discharge the cells to the wells of the microplate.

In a preferable embodiment, the cells C are discharged simultaneously onto the plurality of wells 41 from the plurality of tips 6. FIG. 8 is a diagram for describing an example where the cells C are discharged simultaneously onto the wells 41 of the microplate 4 by a plurality of (three) tips. The wells 41 of the microplate 4 are arranged in an x direction with a uniform pitch x1. The head unit 61 includes three heads 63A, 63B, and 63C. Tips 6A, 6B, and 6C are attached to the heads 63A, 63B, and 63C, respectively. The tips 6A, 6B, and 6C (their front end openings 6H) are disposed in the x direction with a pitch x2 that is twice the pitch x1. The pitch x2 of the tips 6A to 6C is not limited to twice the pitch x1, and thus may be any integral multiple of the pitch x1.

In the sorting container 1, the tips 6A to 6C are caused to suck desired cells C, respectively. Thereafter, the head unit 61 is moved above the microplate 4, and for example, the front end opening 6H of the tip 6A is aligned with one well 41 target for discharge. Since the pitch x2 of the tips 6A to 6C is twice the pitch x1 of the wells 41, the tips 6B and 6C are sequentially aligned with alternate wells 41 in the direction x. Thereafter, the heads 63A to 63C descends. When the front end openings 6H come close to predetermined positions with respect to the wells 41, the cells C are discharged simultaneously from the tips 6A to 6C, respectively. Such simultaneously discharge can reduce the movement time of the head unit 61 and the number of times of up-and-down movements of the heads 63A to 63C, and thus can shorten a time required for the transfer of the cells C.

In the present embodiment, the cell transfer apparatus S that transfers the cells C from the dish 10 to the microplate 4 is provided with a function of distributing the cells C with equivalent quality evenly to the plurality of groups I to V, having specific purposes in the case where the plurality of wells 41 of the microplate 4 to be used are classified into the groups I to V as illustrated in FIG. 7. To achieve the even cell distribution, the cell transfer apparatus S includes:

(1) a function of capturing an image of the dish 10 with the cells C being held by the holding recessed portions 3;

(2) a function of giving evaluation levels to the plurality of cells C held in the dish 10, respectively, based on the image of the dish 10;

(3) a function of allocating transfer destinations of the cells C held in the dish 10 so that the cells C equal in evaluation level are distributed evenly to the plurality of groups in the microplate 4; and (4) a function of transferring the cells C in the dish 10 to the wells 41 in the respective groups in the microplate 4, respectively, based on the allocation. Configurations relating to the functions (1) to (4) of the cell transfer apparatus S will be described below.

[Electrical Configuration of Cell Transfer Apparatus]

Figure 9:
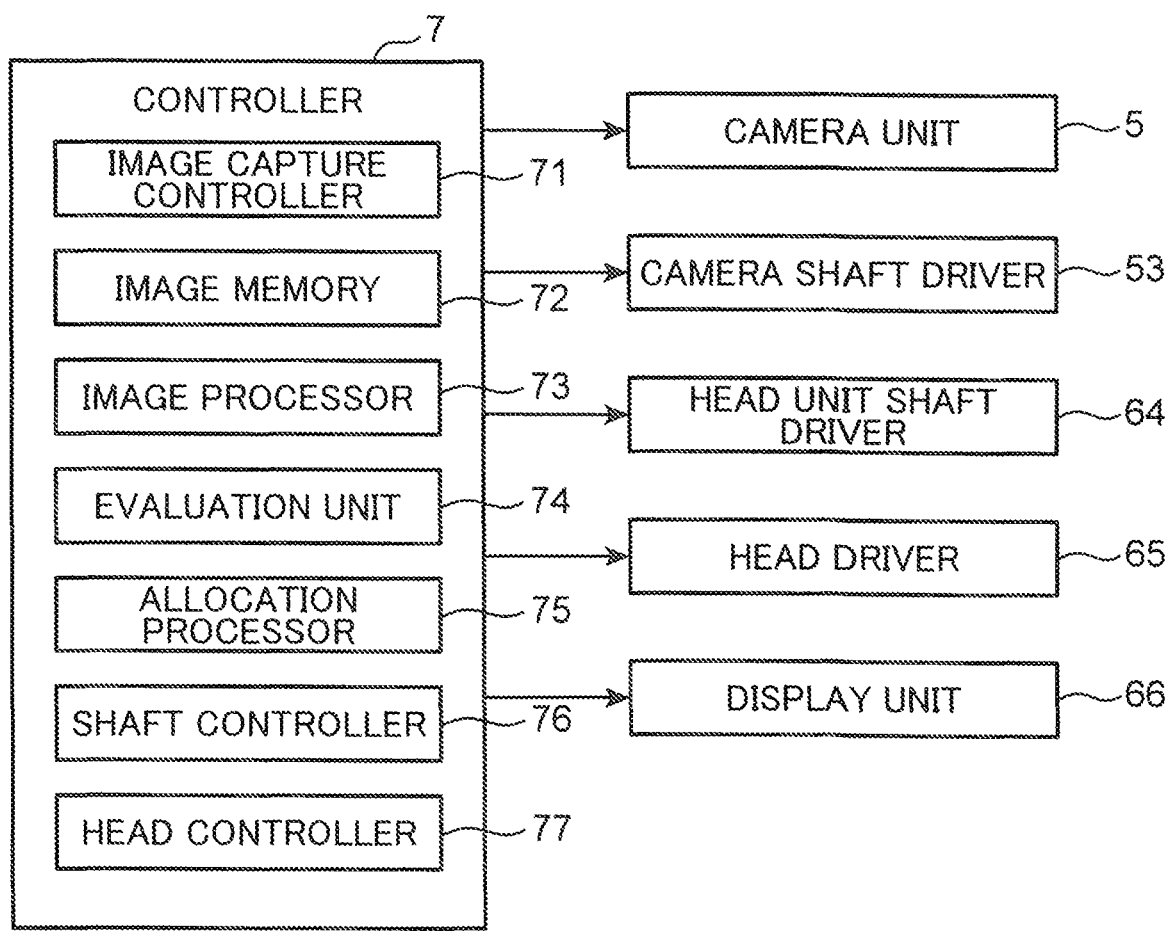
FIG. 9 is a block diagram illustrating an electrical configuration of the cell transfer apparatus.

FIG. 9 is a block diagram illustrating an electrical configuration of the cell transfer apparatus S. The cell transfer apparatus S includes a controller 7 that controls a movement operation of the head unit 61 (FIG. 1), an aligning operation and an up-and-down movement operation of the head 63, an operation for sucking and discharging the cells C by the head 63, and an operation of the camera unit 5. Further, the cell transfer apparatus S includes a camera shaft driver 53 as a mechanism that horizontally moves the camera unit 5, a head unit shaft driver 64 (a part of a transfer unit) as a mechanism that horizontally moves the head unit 61, a head driver 65 (a part of the transfer unit) as a mechanism that causes the head 63 to move up and down and as a mechanism that performs the sucking and discharging operation, and a display unit 66.

The camera shaft driver 53 includes a drive motor that moves the camera unit 5 along the guide rail 52. In a preferable mode, the camera unit 5 that is mounted on a nut member screwed with a ball screw mounted along the guide rail 52 is moved to a target position by the drive motor turning the ball screw in a normal or reverse rotation. Note that although unillustrated in FIG. 1, the camera unit 5 can move also in a direction (a Y direction) orthogonal to the guide rail 52 (an X direction) on a horizontal plane. That is, the camera shaft driver 53 moves the camera unit 5 in the XY direction.

The head unit shaft driver 64 includes a drive motor that moves the head unit 61 (the head main body 62) along the guide rail 61R. In a preferable mode, similarly to the camera shaft driver 53, the head unit shaft driver 64 includes a ball screw and a nut member, and the drive motor turns the ball screw in the normal or reverse direction. Note that when the head main body 62 is moved to two directions, that is, X and Y directions, a first ball screw (the X direction) along the guide rail 61R, and a second ball screw (the Y direction) mounted on a movement board attached to a first nut member screwed with the first ball screw are used. In this case, the head main body 62 is attached to a second nut member screwed with the second ball screw.

The head driver 65 corresponds to the above-described power unit for the ascending and descending mechanism that moves the head 63 in the up and down direction, and a power unit (for example, a motor) that drives the piston mechanism installed into the hollow portion of the head 63 formed by a hollow rod. As described above, the ascending and descending mechanism moves the head 63 up and down between a descending position where the head 63 extends downward from the head main body 62 and an ascending position where most part of the head 63 is accommodated in the head main body 62. The power unit of the piston mechanism causes the piston member disposed in the head 63 to move up and down to generate a suction force and a discharge force in the front end opening 6H of the tip 6 attached to the head 63.

The display unit 66 includes, for example, a liquid crystal display, and displays an image captured by the camera unit 5, and an image subject to an image process executed by the controller 7.

The controller 7 includes, for example, a microcomputer, and includes, as functions, an image capture controller 71, an image memory 72, an image processor 73, an evaluation unit 74, an allocation processor 75, a shaft controller 76 (a part of a transfer controller), and a head controller 77 (a part of the transfer controller).

The image capture controller 71 controls an image capturing operation and a movement operation of the camera unit 5. In the present embodiment, the image capture controller 71 controls at least an operation for causing the camera unit 5 to capture an image of the dish 10 where the cells C are held by the holding recessed portions 3. As described above, since the angle of view of the camera unit 5 is considerably small with respect to the size of the dish 10, the image capture controller 71 causes the camera shaft driver 53 to slightly move the camera unit 5 in the XY direction and simultaneously causes the camera unit 5 to perform the image capturing operation on the dish 10. Further, the image capture controller 71 causes the camera shaft driver 53 to move the camera unit 5 along the guide rail 52 and causes the camera unit 5 to capture an image of the microplate 4.

The image memory 72 includes, for example, a storage region provided in the microcomputer or an external storage, and temporarily stores image data acquired by the camera unit 5.

The image processor 73 processes the image data captured by the camera unit 5 and stored in the image memory 72. The image processor 73 executes, using an image processing technique, a process for recognizing presence of the cells C on the dish 10 through the image, a process for recognizing distribution of the cells C, a process for recognizing shapes of the recognized cells C, and the like, based on, for example, the image of the dish 10 after the cells C are dispensed. Further, the image processor 73 executes a process for recognizing positions of frames (the boundary portions 35) of the holding recessed portions 3 on the upper surface 21, and the like, based on an image of the upper surface 21 of the dish 10.

The evaluation unit 74 executes a process for classifying objects supported by the dish 10 into the cells C that meet a predetermined standard and as cells that fail to meet the standard and foreign substances, based on the image data that has been subject to the image process by the image processor 73, and giving evaluation levels to the cells C that meet the standard. The predetermined standard means, specifically, whether or not the cells are usable cells C (cells that can be used on the microplate 4 for experiments). The evaluation unit 74 executes a process for discriminating such usable cells C from unusable cells and foreign substances. Further, the evaluation unit 74 gives evaluation levels to the usable cells C, respectively, with reference to predetermined multiple-step evaluation levels.

Example of the unusable cells include dead cells, cells having extremely irregular shapes, cells formed by fusing two cells, and cells having color shade clearly different from normal color shade. For example, cells having greatly narrow portions in the middle are likely to be cells formed by fusing two cells. Further, cells having deep color partially or inside are likely to be cells that are dead partially or deep within. The cells are evaluated based on, for example, a deviation of a shape recognized by the image processor 73 from a predetermined template, and a deviation of a recognized cell in an aspect ratio from a reference value. The colors of cells are identified by color tone recognition, namely, evaluated based on, for example, contrast to a reference color. On the other hand, the cells C determined to be usable are evaluated with reference to a predetermined evaluation standard. This evaluation standard is set appropriately in accordance with, for example, types of cells and experimental purposes. Examples of evaluation elements include a size, a shape, and color shade of a cell. The evaluation elements will be described later with reference to an example of FIG. 10. Note that a machine learning method may be employed in the evaluation unit 74 to explicitly teach features on an image of unusable cells and features on an image for defining the evaluation levels of the cells C determined to be usable, to the evaluation unit 74.

The allocation processor 75 executes a process for allocating the cells C to which evaluation levels are given by the evaluation unit 74 into the groups (for example, groups I to V illustrated in FIG. 7) containing the well 41 families of the microplate 4. At this time, the allocation processor 75 fails to perform the allocation process based on an arrangement order of the usable cells C on the dish 10 but sets transfer destinations of the cells C so that the cells C equal in evaluation level are distributed evenly to each of the groups. Note that "even distribution" in the present disclosure includes nearly even distribution in the case where completely even distribution fails to be practically performed.

The shaft controller 76 controls an operation of the head unit shaft driver 64. That is, the shaft controller 76 causes the head unit shaft driver 64 to horizontally move the head unit 61 to a predetermined target position. The shaft controller 76 causes the head unit shaft driver 64 to align the head 63 (the tip 6) with the holding recessed portion 3 of the dish 10 to be subject to a suction operation over the holding recessed portion 3 and to align the head 63 with the well 41 of the microplate 4 to be subject to a discharge operation over the well 41.

The head controller 77 controls the head driver 65. The head controller 77 causes the power unit for the ascending and descending mechanism of the head driver 65 to move the head 63 to be controlled up and down toward a predetermined target position. Further, the head controller 77 controls the power unit of the piston mechanism for the head 63 to be controlled, thus generating a suction force or a discharge force at the front end opening 6H of the tip 6 attached to the head 63 at a predetermined timing. That is, the shaft controller 76 and the head controller 77 cause, based on the setting of the allocation processor 75, the head unit 61 to transfer the cells C held by the holding recessed portions 3 of the dish 10 to the wells 41 in each of the groups in the microplate 4, respectively.

[Evaluation and Allocation of Cells]

Figure 10:
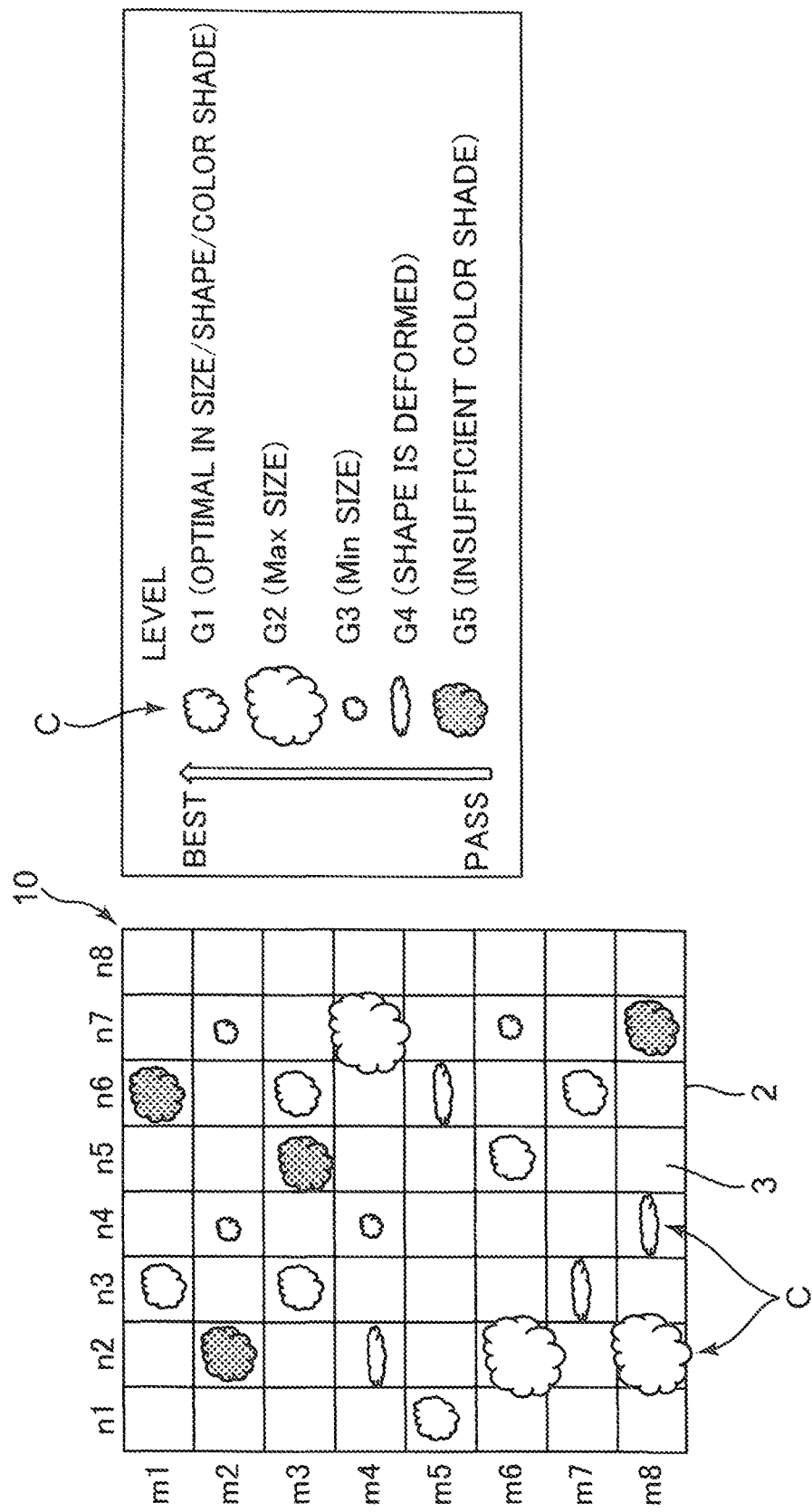
FIG. 10 is a diagram schematically illustrating the cells held in the dish and evaluation levels of the cells.

FIG. 10 is a top view schematically illustrating the cells C held in the dish 10 and an example of evaluation levels of the cells C. The dish 10 illustrated in FIG. 10 corresponds to an image of a state after the dish 10 is immersed in a cell culture solution in the sorting container 1 and the cell culture solution containing the cells C is dispensed. This image captured by the camera unit 5. FIG. 10 omits illustrations of unusable cells and foreign substances, and of a state where two or more cells C are accommodated in one holding recessed portion 3 (the cells C are not to be sucked). FIG. 10 illustrates the dish 10 having the holding recessed portions 3 of 8 rows (m1 to m8)×8 columns (n1 to n8). Some of the sixty-four holding recessed portions 3 accommodate the cells C determined to be usable by the evaluation unit 74.

One example of evaluation levels of the usable cells C is illustrated on the right side of the dish 10 in FIG. 10. Herein, five evaluation levels including levels G1, G2, G3, G4, and G5 are illustrated. The level G1 is given to usable cells C with highest quality (best), and the level G5 is given to usable cells C with lowest quality (pass). The level G1 is given to the cells C, which are samples for a certain experiment, authorized to be most appropriate in size, shape, and color shade. Since the cells C (cell aggregates) in generally good condition each has an approximately spherical shape, a diameter of the cell C can be set as the size. Further, a deformation with respect to the spherical shape can be set as the grade of the shape. The grade of the color shade can be set based on a deviation of the cells C in good condition from natural color.

The level G2 is given to the cells C whose sizes are within a range in which the sizes are larger than the sizes within the range authorized as the level G1 and are smaller than an upper limit in the predetermined usable cell size range. The level G3 is given to the cells C whose sizes are within a range in which the sizes are smaller than the sizes within the range authorized as the level G1 and are larger than a lower limit in the predetermined usable cell size range. The level G4 is given to the cells C whose shapes deviate from a shape range authorized as the level G1 (for example, shapes are close to the spherical shapes) but are irregular within the usable range. The level G5 are given to the cells C whose color shade deviate from a color shade range authorized as the level G1 (for example, the natural color of the cells) but are within the usable color shade range.

The evaluation unit 74 allocates any one of the levels G1 to G5 to each of the cells C held in the dish 10 with reference to the above evaluation level table. Thereafter, the allocation processor 75 executes the allocation process for setting the wells 41 to be the transfer destinations of the cells C in the microplate 4, for the cells C, respectively.

Comparative Example of Allocation Process

Figure 11A:
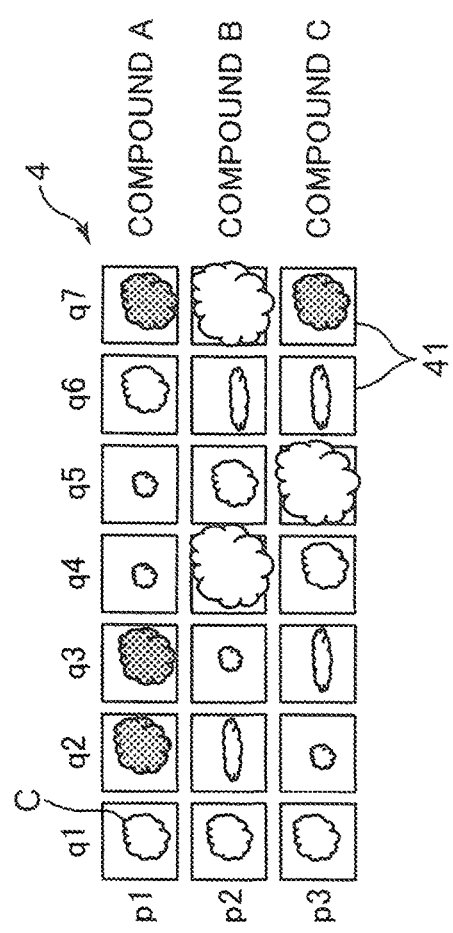
FIG. 11A illustrates an example of assigning numbers to the cells held in the dish.
Figure 11B:
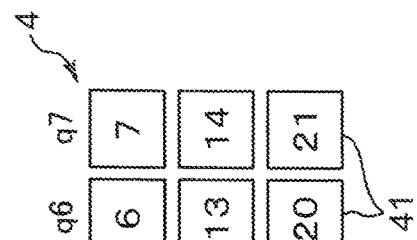
FIG. 11B is a diagram illustrating an order of discharging the cells to the microplate according to a comparative example.
Figure 11C:
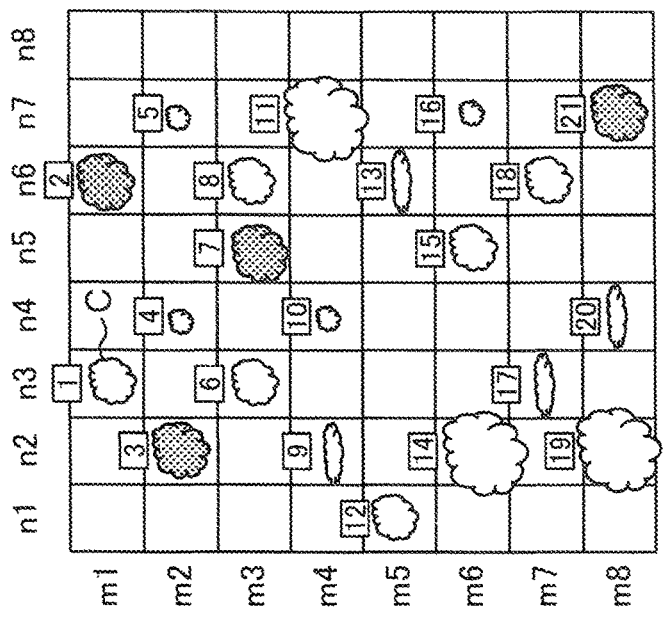
FIG. 11C is a diagram illustrating a situation of the cells discharged to the microplate according to the comparative example.

The allocation process in a comparative example with respect to the present embodiment will be first described with reference to FIGS. 11A to 11C. FIG. 11A illustrates an example of assigning numbers to the cells C held in the dish 10. FIG. 11B is a diagram illustrating an order of discharging the cells C to the microplate 4 (the wells 41). FIG. 11C is a diagram illustrating a situation of the cells C discharged to the microplate 4. The dish 10 and distribution of the supported cells C in FIG. 11A are equal to those illustrated in FIG. 10. FIGS. 11B and 11C illustrate the microplate 4 having the wells 41 of 3 rows (p1 to p3)×7 columns (q1 to q7).

Prior to the allocation, as illustrated in FIG. 11A, the cells C on the dish 10 are assigned numbers. FIG. 11A illustrates an example where the holding recessed portions 3 on the n1 to n8 columns of the m1 row and then the holding recessed portions 3 on the n1 to n8 columns of the m2 row are sequentially scanned. If the held cells C are present, serial numbers are sequentially given to that cells C. In the example of FIG. 11A, 21 usable cells C are supported by the dish 10, and number 1 to 21 are assigned to the cells C. The numbers mean also the order of the suction of the cells C to be performed by the tip 6.

As illustrated in FIG. 11B, in the comparative example, transfer destinations of the 21 cells C are set in accordance with the arrangement order of the wells 41 of 3 rows×7 columns in the microplate 4. That is, the transfer destinations are set for the cells C in the q1 to q7 columns of the p1 row, then the cells C in the q1 to q7 columns of the p2 row, and finally the cells C in the q1 to q7 columns of the p3 row in the numbering order. As illustrated in FIG. 11C, the cells C in the holding recessed portions 3 are transferred to the wells 41 that are the set transfer destinations. For example, since "1" is allocated to the well 41 with address (p1, q1), the cell C which is assigned a number "1" is transferred to the well 41. The cell C which is assigned a number "10" is transferred to the well 41 with address (p2, q3).

In the case of the transfer of the cell C in the comparative example, the cells C with different evaluation levels are randomly arranged on the microplate 4. In an actual use mode of the microplate 4, for example, a cell culture solution containing a compound A is poured into the wells 41 on the p1 row, a cell culture solution containing another compound B into the wells 41 on the p2 row, and a cell culture solution containing still another compound C into the wells 41 on the p3 row. As a result, an experiment can be conducted for reactions of the cells C with the compounds A, B, and C.

However, in uneven distribution of the cells C equal in quality to the p1 row, the p2 row, and the p3 row, sensitivity to the compounds fails to be equally evaluated. For example, the p1 row includes two cells C with the level G1 but includes three cells C with the level G5. On the contrary, the p2 row includes no cell C with the level G5, and thus the quality of the cells C greatly varies among the p1 to p3 rows. For this reason, a determination cannot be made in some cases whether a difference in the reactions to the compounds A, B, and C is derived from original properties of the cells or from a difference in the sensitivities due to unevenness in quality.

Allocation Process According to the Present Embodiment

Figure 12A:
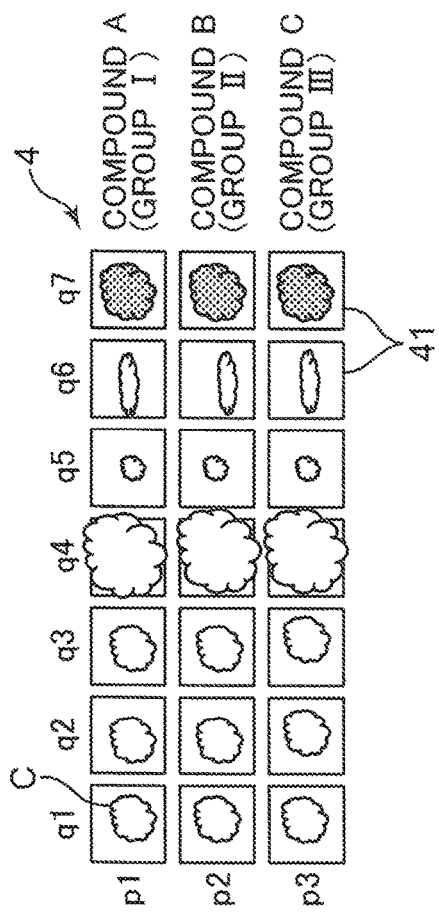
FIG. 12A is a plan view illustrating the cells held in the dish.
Figure 12B:
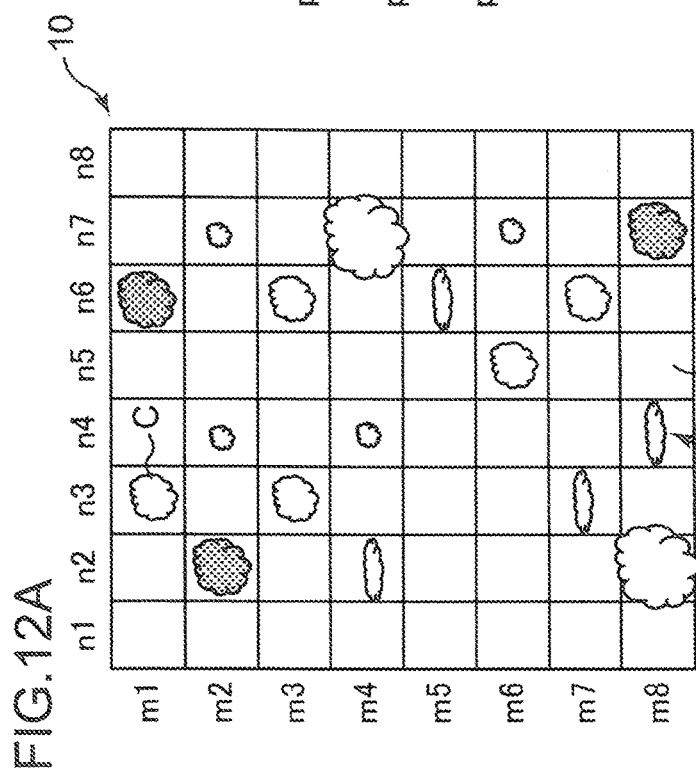
FIG. 12B is a diagram illustrating transfer destinations of the cells to the microplate according to the present embodiment.
Figure 12C:
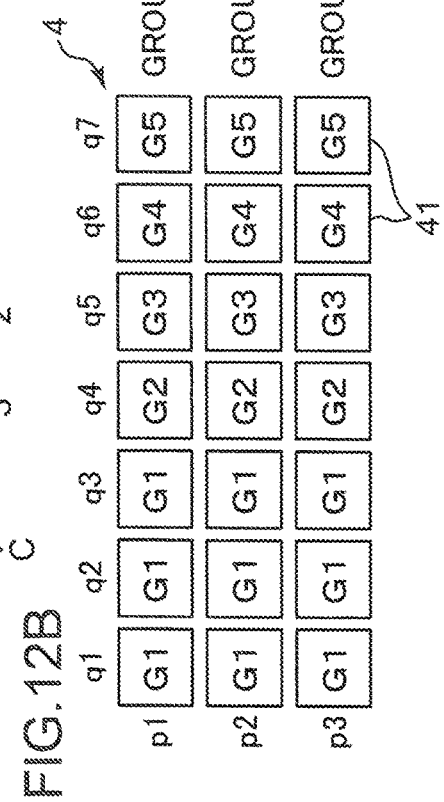
FIG. 12C is a diagram illustrating a situation of the cells discharged to the microplate according to the present embodiment.

The present embodiment can eliminate such a malfunction. FIG. 12A is a plan view illustrating the cells C held in the dish 10. FIG. 12B is diagram illustrating transfer destinations of the cells C to the microplate 4 according to the present embodiment. FIG. 12C is a diagram illustrating a situation of discharging the cells C to the microplate 4 according to the present embodiment. The dish 10 and distribution of the supported cells C illustrated in FIG. 12A are equal to those in FIG. 11A, and arrangements of the wells 41 of the microplate 4 in FIGS. 12B and 12C are also equal to those in FIGS. 11B and 11C.

In the example of FIG. 12A, 21 usable cells C are supported by the dish 10. Although unillustrated, similarly to FIG. 11A, numbers 1 to 21 are assigned to the cells C, respectively. In the present embodiment, the numbers are management numbers of the cells C. The evaluation unit 74 gives the levels G1 to G5 as evaluation levels to the cells C based on the evaluation standard illustrated in FIG. 10. The evaluation unit 74 stores a table illustrated in Table 1 in a storage unit, unillustrated, of the controller 7. Note that if a disposing position of the dish 10 on a work stage is found on an XY coordinate system, an XY dimension may be used instead of a dish address.

TABLE 1

| Level | Management number | Dish address |
|---|---|---|
| G1 | 1 | m1, n3 |
| G1 | 6 | m3, n3 |
| G1 | 8 | m3, n6 |
| ... | ... | ... |
| G2 | 11 | m4, n7 |
| G2 | 14 | m6, n2 |
| G2 | 19 | m8, m2 |

Thereafter, the allocation processor 75 determines which wells 41 of the microplate 4 to accommodate each of the cells C. In the present embodiment, the allocation processor 75 determines the transfer destinations of the cells C so that the cells C equal in evaluation level are distributed evenly to each of the groups into which the plurality of wells 41 in the microplate 4 are classified in advance. In the example illustrated in FIG. 12B, the grouping is carried out in a manner that the wells 41 on the p1 row are in a "group I", the wells 41 on the p2 row are in a "group II", and the wells 41 on the p3 row are in a "group III". Transfer frames depending on the evaluation levels of the cells C are set in the wells 41 in the groups I, II, and III.

In the example of FIG. 12B, the level G1 is assigned to the wells 41 on the q1 to q3 columns. That is, each of the groups I to III has three transfer frames that are to accommodate the best-quality cells C with the level G1. Further, the level G2 is assigned to the wells 41 on the q4 column, the level G3 to the wells 41 on q5 column, the level G4 to the wells 41 on the q6 column, and the level G5 to the wells 41 on the q7 column. That is, each of the groups I to III has one transfer frame that is to accommodate each of the cells C with the levels G2 to G5. Such a configuration enables the cells C with the levels G1 to G5 to be distributed evenly to the well families in the groups I to III.

In this distribution, the usable cells C on the dish 10 are identified, evaluation levels are given to the cells C, and the number of the cells C with each evaluation level is obtained. The number of the cells C with each evaluation level is divided by the number of groups containing the wells 41, and thus an allocating number is set for each group. Naturally, the number of the cells C is indivisible by the number of the groups in some cases, but a processing example of this case will be described later with reference to FIG. 14. The number of the cells C with each evaluation level illustrated in FIG. 12A fails to match a number of each of the allocated evaluation levels in FIG. 12B. That is, in FIG. 12A, only five cells C with the level G1 are present, but simplified illustration in FIG. 12B is based on the assumption that nine cells C with the level G1 are present.

After making the above calculation, the allocation processor 75 adds the associated addresses of the wells 41 to be the transfer destinations of the cells C to the table in Table 1. The allocation processor 75 stores a table illustrated in Table 2 in the storage unit, unillustrated, of the controller 7.

TABLE 2

| Level | Management number | Dish address | Transfer destination address |
|---|---|---|---|
| G1 | 1 | m1, n3 | p1, q1 |
| G1 | 6 | m3, n3 | p2, q1 |
| G1 | 8 | m3, n6 | p3, q1 |
| ... | ... | ... | ... |
| G2 | 11 | m4, n7 | p1, q4 |
| G2 | 14 | m6, n2 | p2, q4 |
| G2 | 19 | m8, m2 | p3, q4 |

The shaft controller 76 moves the head unit 61 with reference to the table in Table 2 and transfers each of the cells C to each of the wells 41 of the specified transfer destination addresses. FIG. 12C illustrates a state after the cells C are transferred to the microplate 4 along the table in Table 2. Three cells C with the level G1 are distributed to each of the groups I to III, and one cell C with a corresponding one of the levels G2 to G5 to each of the groups I to III. That is, the cells C equal in evaluation level are distributed evenly. The groups I to III are classified typically based on a condition of a cell culture solution to be poured into the wells 41. For example, a cell culture solution containing a compound A is poured into the well 41 family in the group I, a cell culture solution containing a compound B into the well 41 family in the group II, and a cell culture solution containing a compound C into the well 41 family in the group III. In this case, since the cells C equal in evaluation level are distributed evenly to the well 41 family in each group, sensitivities become equal, and the equal sensitivities enable reactions of the cells C to the compounds A to C to be accurately evaluated. Note that the wells 41 in each of the groups I to III are not necessarily present in physically close positions, and they may be physically separated from each other as long as each of the same compounds A to C is allocated to the wells 41. Alternatively, the groups I to III may be discriminated based on variations in concentration of the same compound.

An allocation example of simultaneous discharge of the cells C from the plurality of tips 6 to the plurality of wells 41 is illustrated. Herein, the head unit 61 where tips 6A, 6B, and 6C are mounted on three heads 63A, 63B, and 63C, respectively, is assumed as illustrated in FIG. 8. An suction order of the tips 6A to 6C may be set as described in Table 3 below so that the cells C are discharged simultaneously from the three tips 6A to 6C and the cells C with the respective levels are disposed as illustrated in FIG. 12C. In Table 3, the head 63A has head number 1, the head 63B has head number 2, and the head 63C has head number 3. Further, on the assumption that the head unit 61 approaches the dish 10 from left, the suction order is set to be performed in order of the head 63C, the head 63B, and the head 63A (the tip 6C, the tip 6B, and the tip 6A).

TABLE 3

| Level | Management number | Dish address | Transfer destination address | Head number | Suction order |
|---|---|---|---|---|---|
| G1 | 1 | m1, n3 | p1, q1 | 1 | 3 |
| G1 | 6 | m3, n3 | p1, q3 | 2 | 2 |
| G1 | 8 | m3, n6 | p1, q2 | 1 | 6 |
| ... | ... | ... | | | |
| G2 | 11 | m4, n7 | p1, q4 | 2 | 5 |
| G2 | 14 | m6, n2 | p2, q4 | | |
| G2 | 19 | m8, n2 | p3, q4 | | |
| ... | ... | ... | | | |
| G3 | 4 | m2, n4 | p1, q5 | 3 | 1 |
| ... | ... | ... | | | |
| G4 | 9 | m4, n2 | p1, q6 | 3 | 4 |

According to a sequence in Table 3, in first-cycle suction where all the tips 6C to 6A of the three heads 63C to 63A sequentially suck the cells C (the suction order 1 to 3), the tip 6C sucks the cell C with the level G3, the tip 6B and the tip 6A suck the cells C with the level G1. The transfer destination addresses in Table 3 are determined with consideration to the pitch x2 of the tips 6A to 6C being twice the pitch x1 of the wells 41. Therefore, the simultaneous discharge of the cells C sucked in the first cycle to the microplate 4 causes the cells C with the respective levels according to the arrangement in FIG. 12C to be accommodated in the wells 41 on the q1, q3, and q5 columns of the p1 row, respectively. Further, in second-cycle suction (suction order 4 to 6), the tip 6C sucks the cell C with the level G4, and the tip 6B sucks the cell C with the level G2, and the tip 6A sucks the cell C with the level G1. The simultaneous discharge of the cells C to the microplate 4 causes the cells C with the respective levels according to the arrangement in FIG. 12C to be accommodated in the wells 41 on the q2, q4, and q6 columns of the p1 row, respectively. Much the same is true on the subsequent cycles. As illustrated in FIG. 12C, the arrangement of the cells C with the respective levels in the correct order provides an advantage such that medicinal effects can be checked by the levels of the cells C at a glance.

MODIFIED EXAMPLES

Figure 13:
FIG. 13 is a diagram for describing a first modified example of the present embodiment.

FIG. 13 is a diagram for describing a first modified example of the present embodiment. FIG. 13 illustrates an example where a control group is added to the above-described groups I to III when the plurality of wells 41 of the microplate 4 are classified into groups. In the example of FIG. 13, the well 41 families on the p1 to p3 rows are classified into the groups I to III, and the well 41 family on the pr row is classified into the control group. Similarly to the above embodiment, the cells C equal in evaluation level are distributed evenly to each of the groups I to III. On the other hand, only the cells C with the best level G1 are distributed to the control group.

The control group is used as, for example, an area that contains no compound (a non-compound area). For example, in experiment for checking the compounds poured into the groups I to III for a medicinal effect of killing the cells C, provision of the non-compound area enables the check to be made whether the cells C are dead due to the medicinal effect or are naturally dead. Alternatively, the control group can be used as an area where a blending amount and a composition that might securely cause the death of the cells C can be checked by pouring a medicine compound whose blending is estimated to produce a powerful medicinal effect into the wells 41 in the control group. On the contrary, the control group can be used also as the area where a blending amount and a composition that secure the survival of the cells C can be checked by pouring a medicine compound whose blending is estimated to produce no medicinal effect into the wells 41 in the control group. Quality of the cells C to be accommodated in the control group is determined as desired based on an experiment purpose. For example, as illustrated in FIG. 13, the cells C with average levels (for example, the cells C with the levels G2 and G3) may be accommodated in the control group instead of the cells C with the best level G1. Needless to say, the cells C that are equal in level to the groups I to III can be distributed to the control group.

FIG. 14 is a diagram for describing a second modified example of the present embodiment. FIGS. 12B and 12C illustrate the simple example where the number of cell groups with each of the evaluation levels is exactly divisible by the number of the groups. That is, in such an example, in a case where the evaluation levels include a first level (the level G1) and a second level (G2) lower in grade than the first level, and the plurality of groups include n groups, the allocation processor 75 allocates the allocation processor allocates, to each of the plurality of groups, a/n pieces of transfer destination addresses and b/n pieces of transfer destination addresses when "a" pieces of the cells C with the first level exist, and "b" pieces of the cells C with the second level exist. Specifically, FIGS. 12B and 12C illustrate the example where nine cells C with the level G1 and three cells C with each of the levels G2 to G5 lower in grade than the level G1 are present, three groups are present on the microplate 4, and 9/3 transfer destination addresses for the cells C with the level G1 and 3/3 transfer destination addresses for the cells C with each of the levels G2 to G5 are allocated to each of the groups I to III.

On the contrary, FIG. 14 illustrates an example of a process for evenly distributing the cells C when the number of the cells C is indivisible by the number of the groups. In this case, the allocation processor 75 sets a first group (in FIG. 14, the group III on the p3 row) to which the cells C with the first level (the level G1) are distributed, the number of the cells C being the quotient of a/n, and second groups (the groups I and II on the p1 and p2 rows) to which the cells C are distributed, the number of the cells C being obtained by adding each of remainders of a/n to the quotient. The allocation processor 75 then allocates the cell C with the second level (the level G2) preferentially to a transfer destination address (p3, q4) where a shortfall of the cell C with the first level occurs in the first group. The allocation processor 75 executes the similar allocating process also for the lower-grade levels (the levels G2 to G5).

FIG. 14 illustrates an example where the number of the cells C is 11 for the level G1, 8 for the level G2, 9 for the level G3, 6 for the level G4, 8 for the level G5, and a number n of the groups in the microplate 4 is 3. The distribution of the cells C is determined starting from address (p1, q1) and in order of the q1 column, the q2 column ... the q14 column. In the above distributing method, the allocation of the cells C with the best level G1 is set by the following calculation:

a/n=11/3=3 remainder 2. First, one group is provided to which the three cells C with the level G1 are allocated, three being the number of the quotients. Two groups are provided to which the four cells C with the level G1 are allocated, four being obtained by adding each of the remainders 2 to 3 that is the quotient. FIG. 14 illustrates an example where the four cells C with the level G1 are distributed to each of the groups I and II, and the three cells C with the level G1 are distributed to the residual group III.

The number of the cells C with the best level G1 to be allocated is smaller by 1 in the group III than those in the groups I and II. For this reason, the cells C with the level G2 second higher in grade after the level G1 are preferentially allocated to the group III. That is, the biggest number of the cells C with the level G2 can be allocated to the group III. Therefore, the cell C with the level G2 is allocated to address (p3, q4). On the q5 and subsequent columns, the cells C with the level G2 are first allocated to the p3 row in the group III. Since the eight cells with the level G2 are present, the cell C with the level G2 is allocated only to the p3 row of the q7 column. Such an allocation method enables the preferential allocation of the cells C with the level G2 to cover a shortfall of the cell C with the level G1 in group III, and thus can achieve equalization among the groups.

The cells C with the level G3 are allocated preferentially to the group I or II. FIG. 14 illustrates an example where the p2 row in the group II has priority, and the cell C with the level G3 is allocated only to the p2 row of the q10 column. The cells C with the level G4 are allocated preferentially to the p1 row in the group I, and the cell C with the level G4 is distributed only to the p1 row of the q12 column. The cells C with the level G5 are allocated to the residual wells 41. In such a manner, the equalizing process similar to the equalization between the levels G1 and G2 is executed in the allocation of the cells C with the level G2 and the subsequent levels.

The process in the case where the number of the cells C is indivisible by the number of the groups can be applied also to a case where the number of the cells C is smaller than the number of the groups. For example, the number of the cells C with the level G1 is 11, whereas the number of the groups n in the microplate 4 is 13. In this case, the cells C with the level G1 fails to be allocated to the two groups. For this reason, the cells C with the level G2 may be allocated preferentially to the two groups (the biggest number of the cells C with the level G2 may be allocated).

[Description of Operation Flow of Cell Transfer Apparatus]

Figure 15A:
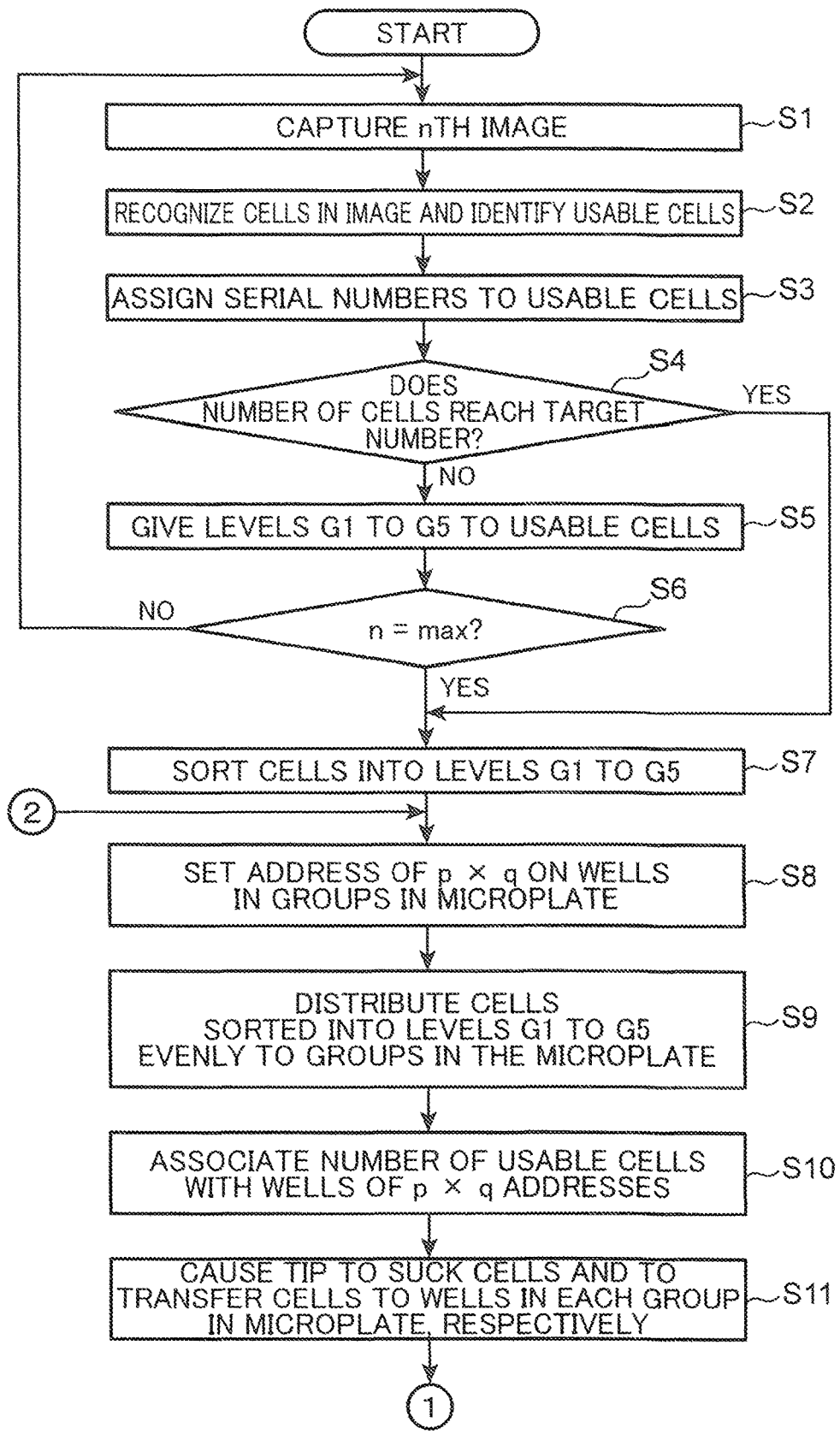
FIG. 15A is a flowchart illustrating an operation of the cell transfer apparatus.
Figure 15B:
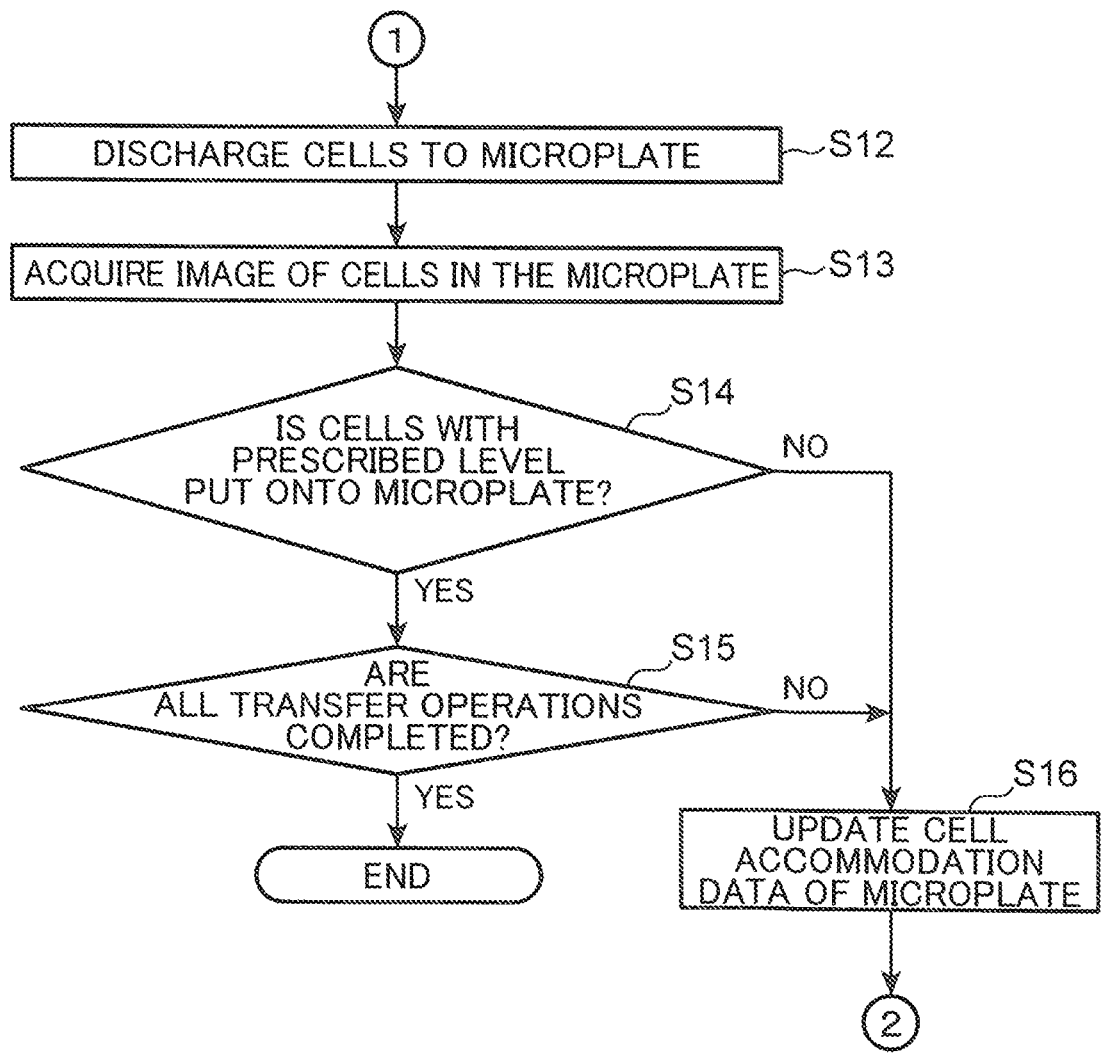
FIG. 15B is a flowchart illustrating an operation of the cell transfer apparatus.

FIG. 15A and FIG. 15B are flowcharts illustrating an example of an operation of the cell transfer apparatus S. As illustrated in FIG. 1, the plurality of cells C dispersed in the cell culture solution are put into the sorting container 1, and the cells C are held on the dish 10. First, the dish 10 in which the cells C are held is imaged. The image capture controller 71 causes the camera shaft driver 53 to move the camera unit 5 to an imaging position below the sorting container 1, namely, an nth image capture position. For example, in the image capturing range AV (FIG. 5) of the camera unit 5, when one-hundred image capturing operations are required for imaging an entire imaging area of the dish 10, the camera shaft driver 53 moves the camera unit 5 to a 1/100th (n=1) image capture position. The image capture controller 71 then causes the camera unit 5 to execute the image capturing operation (step S1). Image data acquired by the image capturing is stored in the image memory 72.

A process for identifying usable cells C from objects supported by the dish 10 is executed (step S2). Specifically, the image processor 73 executes an image process on the image data of the dish 10, and the evaluation unit 74 executes a determining process for the cells C. The image processor 73 executes a process for recognizing presence of the cells C on the dish 10 through images, and executes a process for recognizing shapes of the recognized cells C. The evaluation unit 74 executes a process for classifying the objects supported by the dish 10 into the cells C that meet a predetermined standard and as cells that fail to meet the standard and foreign substances, based on the image data that has been subject to the recognizing process by the image processor 73.

The evaluation unit 74 then assigns serial numbers to be management numbers (numbering) to the usable cells C, which meet the predetermined standard, on the dish 10 (step S3). This numbering is as described with reference to FIG. 11A. Herein, the evaluation unit 74 assigns numbers also to cells that determined to be unusable except for foreign substances, and may execute a statistical process for taking statistics on, for example, a usable rate of the cells C dispersed on the dish 10.

Thereafter, the evaluation unit 74 determines whether the number of the cells C to be transferred to the microplate 4 reaches a target number (step S4). That is, the evaluation unit 74 determines whether a sufficient number of the cells C required for providing the cells C with a target level can be acquired for all the wells 41 to accommodate the cells C in the microplate 4. If the target number of the cells C fail to be yet acquired (NO in step S4), the process proceeds to next step S5, and if the target number of the cells C can be acquired (YES in step S4), the process skips to step S7.

Thereafter, the evaluation unit 74 executes a process for giving the levels G1 to G5 as the evaluations levels to the cells C with the management numbers, based on, for example, the evaluation standard illustrated in FIG. 10 (step S5). Further, the evaluation unit 74 creates a table, as illustrated in Table 1, where the management numbers, the dish addresses of the holding recessed portions 3 as the holding positions for the cells C, and the evaluation levels are related to each other.

After that operation, the evaluation process for one captured image is completed. Thereafter, the evaluation unit 74 determines whether a number of image capture times n reaches a predetermined number of times (Max) (step S6). If the number of image capture times n fails to reach the Max number of times (NO in step S6), the process returns to step S1, image capturing is performed in a next capture position, and the same process is repeated. As described above, when the one hundred image capturing operations are necessary for covering the entire dish 10, the same operation is repeated at one hundred times.

If the number of capturing times n reaches Max (YES in step S6), the evaluation unit 74 integrates tables obtained on the respective capture positions and sorts the cells C into the levels G1 to G5 with reference to the table data (step S7). As a result, for example, a table is created by sorting all the cells C determined to be usable by the one hundred image capturing operations and the image process into the level G1 to G5. At this time point, the number of the cells C with each of the levels G1 to G5 on the dish 10 is acquired.

Thereafter, the allocation processor 75 sets transfer destinations addresses, which are the transfer destinations of the cells C, for the wells 41 in each group in the microplate 4 (step S8). The addresses are set into, for examples, p rows×q columns illustrated in FIG. 12B. FIG. 12B illustrates an example where the groups I to III are formed in each row, but the groups may be formed by predetermined area unit of p rows×q columns. In this case, the address setting may be performed by assigning serial numbers in each area.

The allocation processor 75 executes the allocation process for setting transfer destinations of the cells C sorted into the levels G1 to G5 so that the cells C with equal in evaluation level are distributed evenly to each of the groups in the microplate 4 (step S9). This allocation process is as described with reference to FIGS. 12B and 12C or FIG. 13. Further, in the case where the number of cell families with the evaluation levels is indivisible by the number of the groups, the allocation process for approaching completely even distribution as close as possible is as described with reference to FIG. 14.

At the end of the allocation process, the allocation processor 75 associates the management numbers of the usable cells C with the addresses of the wells 41 to be the transfer destinations of the cells C, and creates a table as illustrated in Table 2 (step S10). The shaft controller 76 and the head controller 77 perform an operation for sucking the cells C from the dish 10 and an operation for moving the head unit 61 with reference to the table created by the allocation processor 75 (step S11).

As illustrated in FIG. 15B, at the completion of the movement of the head unit 61 to a predetermined position in the microplate 4, the head controller 77 causes the cell C to be discharged from the tip 6 to the well 41 with the specified transfer destination address (step S12).

Thereafter, the image capture controller 71 causes the camera unit 5 to perform an operation for capturing an image of the cell C transferred to the microplate 4 (step S13). The image processor 73 executes the image process on the acquired image data, and determines whether the cells C with the specified level are accommodated in the wells 41 with specified addresses (step S14). This prevents false suction or false discharge of the cells C.

If the cells C with the levels are accommodated in the specified addresses on schedule (YES in step S14), a determination is made whether the transfer of all the cells C which are assigned the numbers is completed (step S15). If the transfer of all the cells C is completed (YES in step S15), the controller 7 ends the process.

If the cells C with the respective levels are not accommodated in the specified addresses on schedule (NO in step S14), cell accommodation data of the microplate 4 is updated based on an actual accommodation situation (step S16). The cell accommodation data indicates correspondence between the cells C with the respective levels and the wells 41, which actually accommodate the cells C, respectively, in the microplate 4. For this reason, if the cells C are transferred on schedule (YES in step S14) and the transfer of all the cells C is not completed (NO in step S15), the cell accommodation data is updated so that the completed transfer of the cells C on schedule is reflected on that data (step S16). Thereafter, the process returns to step S8, and step S8 and subsequent steps are executed based on the updated cell accommodation data.

Modified Example of Simultaneous Discharge of Cells

As a third modified example, an example where the head unit 61 includes a plurality of tips 6 that sucks and discharges the cells C will be described. This example refers to simultaneous discharge from the tips 6 to the plurality of wells 41 of the microplate 4. For example, simultaneous discharge using the head unit 61, illustrated in FIG. 8, mounted with three tips 6A, 6B, and 6C disposed in a line (a predetermined arrangement state) can greatly shorten a time required for transferring the cells C.

Figure 16:
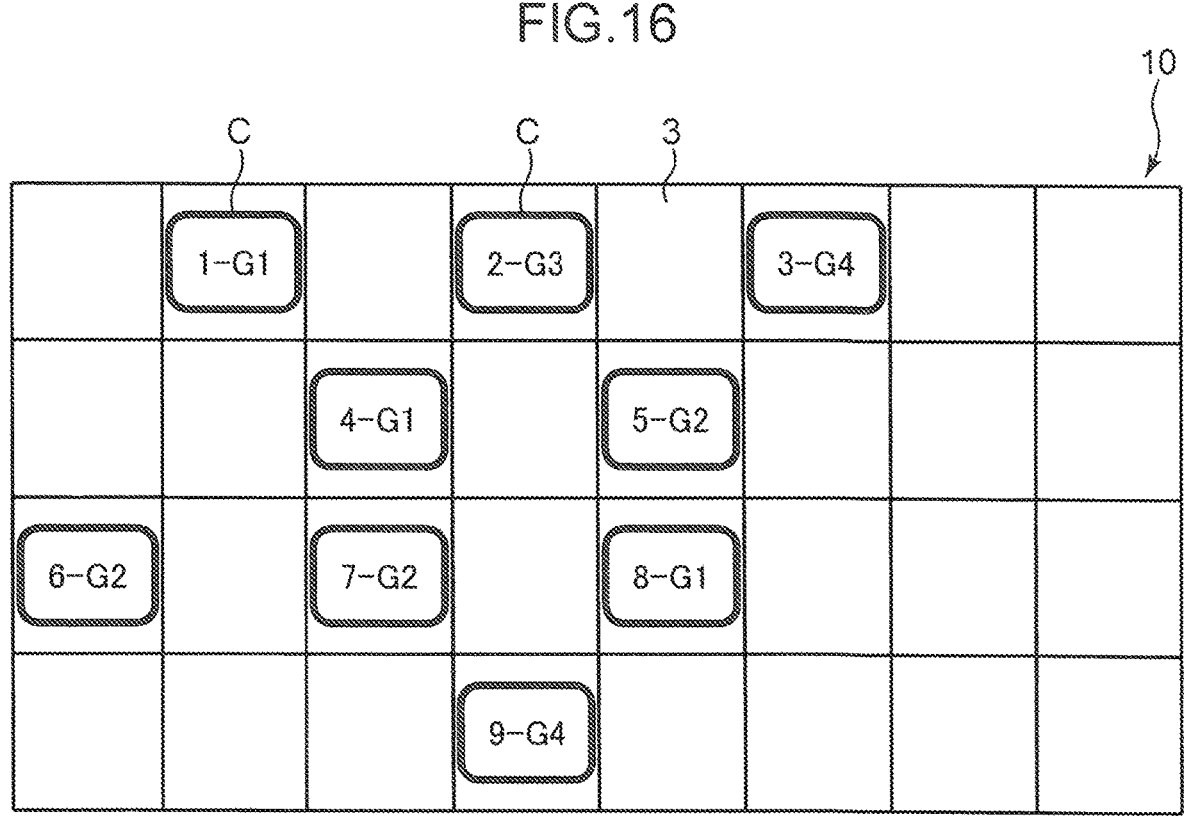
FIG. 16 is a diagram schematically illustrating the cells held in the dish and levels of the cells.

FIG. 16 is a diagram schematically illustrating the cells C held by the holding recessed portions 3 of the dish 10 and evaluation levels of the cells C. FIG. 16 indicates serial numbers that are sequentially assigned to the held cells C in order of suction using the tips 6, and the evaluation levels G1 to G4. For example, "1-G1" means the cell C that has the level G1 and is to be first sucked and, "7-G2" means the cell C that has the level G2 and is to be seventhly sucked.

In the case where the head unit 61 having the three tips 6A, 6B, and 6C sucks the cells C from the dish 10, the cells C are sucked by the tips 6A to 6C, respectively, in one sucking operation as follows:
first suction="1-G1", "2-G3", "3-G4";
second suction="4-G1", "5-G2," "6-G2"; and
third suction="7-G2", "8-G1", "9-G4".

FIG. 17 is a pattern diagram illustrating an example of allocating the cells C evenly to the microplate 4. In this example, in the microplate 4 having the wells 41 of 3 rows (p1 to p3)×eight columns (q1 to q8), the wells 41 on the p1 row are in "group I", the wells 41 on the p2 row are in "group II", and the wells 41 on the p3 row are in "group III". For example, in the allocation process in step S8 of FIG. 15, the q1 and q2 columns are allocated to the cells C with the level G1, the q3 and q4 columns are allocated for the cells C with the level G2, the q5 and q6 columns for the cells C with the level G3, and the q7 and q8 columns for the cells C with the level G4 in each of the groups I to III.

Figure 18:
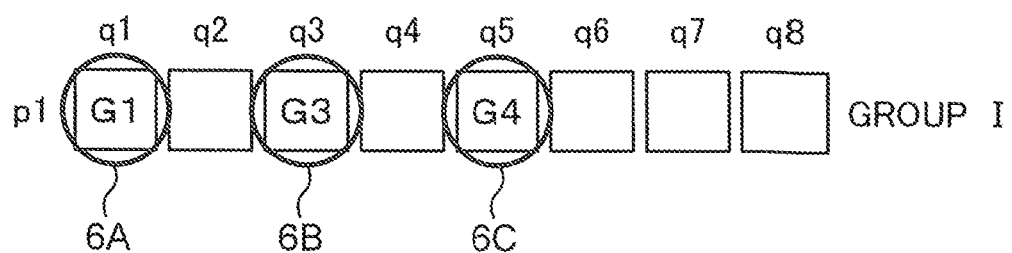
FIG. 18 is a diagram describing a third modified example according to the present embodiment.

As illustrated in FIG. 8, the arrangement pitch x2 of the three tips 6A, 6B, and 6C disposed in a line is assumed to be twice the arrangement pitch x1 of the wells 41. In this case, even though the cells C "1-G1", "2-G3", and "3-G4" held in the tips 6A to 6C by the first suction are tried to be discharged simultaneously to the microplate 4, the cells C do not match any allocation in FIG. 17. For example, as illustrated in FIG. 18, when the cells C first sucked to the p1 row in the group I are simultaneously discharged, the cell C with G1 is discharged to the well 41 with address (p1, q1), the cell C with G3 to the well with address (p1, q3), and the cell C with G4 to the well 41 with address (p1, q5). Therefore, the discharge pattern does not match the level allocation in FIG. 17.

For this reason, the discharge of the cells C held by the first suction requires an operation for aligning the tip 6A with the well 41 with address (p1, q1), and causing the head 63A to move down, discharge the cells from the tip 6A, and causing the head 63A to move up, an operation for moving the head unit 61 so that the tip 6B aligns with the well 41 with address (p1, q5), and causing the head 63B to move down, discharge the cells from the tip 6B, and causing the head 63B to move up, and an operation for moving the head unit 61 so that the tip 6C aligns with the well 41 with address (p1, q7) and causing the head 63C to move down, discharge the cells from the tip 6C, and to move up. Such individual operations for discharging the cells C from the tips 6A to 6C take a long time.

Therefore, to enable simultaneous discharge of the cells C from the tips 6A to 6C, the allocation processor 75 executes a processor for resetting transfer destinations of the cells C within a setting range where the cells C equal in evaluation level are distributed evenly to each of the groups I to III. Specifically, upon acquisition of the order of sucking the cells C and the evaluation levels illustrated in FIG. 16, the allocation processor 75 changes the allocation for each level in each of the groups within a range of the even allocation frame illustrated in FIG. 17 so that simultaneous discharge is enabled.

In the example of the even allocating in FIG. 17, two cells C with each of the levels G1 to G4 are allocated in this order to the wells 41 on the q1 to q8 columns in each of the groups I to III. For example, in the group I, the level for the address (p1, q3) is changed from the level G2 to the level G3, and the level for the address (p1, q5) is changed from the level G3 to the level G4 (the level G1 for the address (p1, q1) is left unchanged) as illustrated in FIG. 18.

Figure 19A:
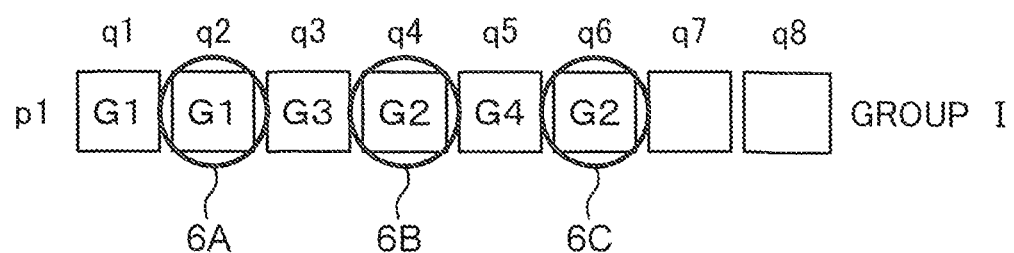
FIGS. 19A and 19B are diagrams describing the third modified example according to the present embodiment.
Figure 19B:
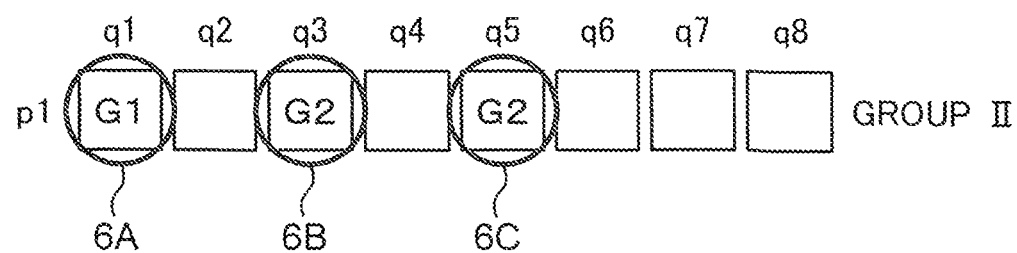

In the second suction, the cells C "4-G1", "5-G2", and "6-G2" are held in the tips 6A to 6C, respectively. For this reason, in the case of the second discharge to the wells 41 in the group I, as illustrated in FIG. 19A, the level for the address (p1, q6) is changed from the level G3 to the level G2 (the level G1 for the address (p1, q2) and the level G2 for the address (p1, q4) are left unchanged). In the case of the second discharge to the wells 41 in the group II, as illustrated in FIG. 19B, the level for the address (p2, q6) is changed from the level G3 to the level G2 (the level G1 for the address (p2, q1) and the level G2 for the address (p2, q3) are left unchanged). In such a manner, the resetting the transfer destinations of the cells C with the respective levels enables the simultaneous discharge from the tips 6A to 6C and can improve the operation efficiency.

The transfer destinations of the cells C may be reset within a range of the number of the respective levels allocated evenly into the respective groups I to III so that the cells C can be discharged simultaneously from the three (the plurality of) tips 6A to 6C for preference. Discharge is performed individually on the wells 41 with addresses that cannot be covered by the simultaneous discharge. For example, in the example of FIG. 19(A), the levels G3 and G4 are one short of the required number "2" in the level G1 to G4 allocated to the group I. Therefore, for example, the level G3 is allocated to the address (p1, q7) and the level G4 to the address (p1, q8). Thus, the cells C are discharged individually to the addresses. Note that the simultaneous discharge is performed not only to the same group, and thus may be performed across a plurality of groups.

In the cell transfer apparatus S according to the present embodiment, the evaluation unit 74 of the controller 7 gives evaluation levels to the plurality of cells C held by the holding recessed portions 3, respectively, on the dish 10 as the transfer source of the cells C. This makes it clear how many cells C with what quality are held in the dish 10. Thereafter, the allocation processor 75 sets the transfer destinations of the cells C on the dish 10 so that the cells C equal in evaluation level are distributed evenly to each of the groups I to III set in the microplate 4. Accordingly, this setting, for example, prevents the cells C with high evaluation level or the cells C with low evaluation level from being distributed unevenly to a specific group in the microplate 4. Therefore, use of the cell transfer apparatus S enables various processes to be executed on the cells C without irregular quality among the groups I to III.

Note that the "evaluation level" has various meanings in the present disclosure. The above-described embodiment refers to the example where the evaluation level is divided into the five levels G1 to G5 based on solely a heuristic quality check for shapes and color shade of the cells C. The evaluation level may include physically measurements of the cells C. For example, measurements of sphericity and color shade of the cells C may be treated as the evaluation level. This case is useful to a situation where resolution of measurements is not that high. On the other hand, when measurements with comparatively high resolution are used as the evaluation levels, "equal evaluation level" is divided too finely. In such a case, measurements of the plurality of cells C are classified by a predetermined range unit, and a family of the cells C in a certain predetermined range can be regarded to have "equal evaluation level". That is, a concept of "equal evaluation level" can be set appropriately depending on a situation of the cells C.

Note that the above-described specific embodiments mainly include the disclosure having the following configurations.

One aspect of the present disclosure provides a cell transfer apparatus including a dish having a plurality of holding portions holding a plurality of cells to be transferred, respectively, a microplate having a plurality of wells that receive the cells, the plurality of wells being classified into a plurality of groups, a transfer unit that transfers the cells from the dish to the microplate, an imaging unit that captures an image of the dish with the cells being held by the plurality of holding portions, an evaluation unit that gives evaluation levels to the cells held in the dish, respectively, based on the image of the dish, an allocation processor that sets transfer destinations of the cells on the dish so that the cells equal in evaluation level are distributed evenly to each of the plurality of groups in the microplate, and a transfer controller that causes the transfer unit to transfer the cells held by the holding portions of the dish to the plurality of wells in the plurality of groups in the microplate, respectively, based on the transfer destinations set by the allocation processor.

Another aspect of the present disclosure provides a cell transfer method for transferring a cell held in a dish to a microplate where a plurality of wells are classified into a plurality of groups, the cell transfer method including capturing an image of the dish in which the cell to be transferred is held, giving evaluation levels to the plurality of the cells held in the dish, respectively, based on the image of the dish with reference to predetermined multiple-step evaluation levels for the cells, setting transfer destinations of the plurality of the cells on the dish so that the cells equal in evaluation level are distributed evenly to each of the plurality of groups in the microplate, and transferring the plurality of the cells held in the dish to the plurality of wells in the plurality of groups in the microplate, respectively, based on the setting of the transfer destinations.

In the cell transfer apparatus or the cell transfer method, the evaluation unit first gives evaluation levels to the plurality of cells held on the dish as a transfer source of the cells. This makes it clear how many cells with what quality are held in the dish. Thereafter, the allocation processor sets transfer destinations of the cells on the dish so that the cells equal in evaluation level are distributed evenly to each of the groups in the microplate. Accordingly, this setting, for example, prevents the cells with high evaluation level or the cells with low evaluation level from being distributed unevenly to a specific group in the microplate. For this reason, various processes can be executed on the cells without irregular quality among the groups.

In the cell transfer apparatus, the evaluation unit desirably classifies the cells into cells that meet a predetermined standard and cells that fail to meet the predetermined standard and foreign substances, based on the image of the dish, and gives the evaluation levels to the cells that meet the predetermined standard.

Before giving the evaluation levels, the cell transfer apparatus can discriminate the cells to be transferred, namely, can classify the cells into usable cells and the other cells. This classification can suppress irregularity of the quality of the cells to be transferred to the microplate.

In the cell transfer apparatus, it is desirable that a culture solution is poured into the plurality of wells of the microplate, and the plurality of groups are classified based on a condition of the culture solution.

When the plurality of groups are formed by varying a condition of a culture solution, such as a compound to be added, the cell transfer apparatus can equally evaluate sensitivities to the compounds because the cell quality is made to be uniform among the groups.

In the cell transfer apparatus, it is desirable that in a case where the evaluation levels include a first level and a second level lower in grade than the first level, and the plurality of groups include n groups, the allocation processor allocates, to each of the plurality of groups, a/n pieces of transfer destination addresses and b/n pieces of transfer destination addresses when "a" pieces of the cells with the first level exist "b" pieces of the cells with the second level exist.

This cell transfer apparatus can execute, according to simple logic, the process for distributing the cells with the first and second levels different in grade from each other evenly to each of n groups in the microplate.

In the cell transfer apparatus, it is desirable that when "a" is indivisible by "n", the allocation processor sets a first group to which the cells with the first level are distributed, a number of the cells being a quotient of a/n, and a second group to which the cells are distributed a number of the cells being obtained by adding each of remainders of a/n to the quotient, and allocates the cells with the second level preferentially to transfer destination addresses where a shortfall of the cells with the first level occurs in the first group.

The cell transfer apparatus can allocate the cells with the second highest level after the first level preferentially to a group where "a" is indivisible by n (including the case where "a" is smaller than "n") and the number of the cell with the first level with the highest level is smaller by 1 than those in other groups. Therefore, even when "a" is indivisible by "n", the quality can be made to be as uniform as possible among the groups.

In the cell transfer apparatus, it is desirable that the transfer unit includes a plurality of tips that can suck and discharge the cells, in a predetermined arrangement state, the plurality of tips being configured to suck the cells in the holding portions and discharge the cells to the plurality of wells, and the allocation processor resets, within a setting range, transfer destinations of the cells so that the cells can be discharged simultaneously from the plurality of tips to the plurality of wells, the setting range being a setting range where the cells equal in evaluation level are distributed evenly to each of the plurality of groups.

The cell transfer apparatus can discharge the cells sucked from the dish by the plurality of tips simultaneously from the plurality of tips to the wells of the microplate. This simultaneous discharge can improve the operation efficiency of the cell transfer.

According to the present disclosure described above, the cell transfer apparatus that transfers the cells from the dish holding the cells to the microplate having the wells for receiving the cells enables the cells with equivalent quality to be distributed evenly to the wells in each of the plurality of groups. This distribution enables various processes to be executed on cells without irregular quality among the groups, and thus enables acquisition of processed results with high accuracy.

What is claimed is:

1. A cell transfer apparatus comprising:
    a dish having a plurality of holders configured to hold a plurality of cells to be transferred;
    a microplate having a plurality of wells configured to receive the cells, the plurality of wells being classified into a plurality of groups;
    a cell transfer head configured to transfer the cells from the dish to the microplate;
    an imager configured to capture an image of the dish with the cells being held by the plurality of holders;
    an evaluation circuit configured to assign evaluation levels to the cells held in the dish, respectively, based on the image of the dish;
    an allocation processor configured to set transfer destinations of the cells on the dish so that the cells equal in evaluation level are distributed evenly to each of the plurality of groups in the microplate; and
    a transfer controller configured to control the cell transfer head to transfer the cells held by the holders of the dish to the plurality of wells in the plurality of groups in the microplate, respectively, based on the transfer destinations set by the allocation processor.

2. The cell transfer apparatus according to claim 1, wherein the evaluation circuit is configured to classify the cells into cells that meet a predetermined standard and cells that fail to meet the predetermined standard and foreign substances, based on the image of the dish, and to assign the evaluation levels to the cells that meet the predetermined standard.

3. The cell transfer apparatus according to claim 1, wherein
    a culture solution is poured into the plurality of wells of the microplate, and
    the plurality of groups are classified based on a condition of the culture solution.

4. The cell transfer apparatus according to claim 1, wherein
    in a case where the evaluation levels include a first level and a second level lower in grade than the first level, and the plurality of groups include n groups, the allocation processor is configured to allocate, to each of the plurality of groups
    a/n pieces of transfer destination addresses and b/n pieces of transfer destination addresses when "a" pieces of the cells with the first level exist and "b" pieces of the cells with the second level exist, and
    when "a" is indivisible by "n",
    the allocation processor is configured to
        set a first group to which the cells with the first level are distributed, a number of the cells being a quotient of a/n, and a second group to which the cells are distributed, a number of the cells being obtained by adding each of remainders of a/n to the quotient, and
        allocate the cells with the second level preferentially to transfer destination addresses where a shortfall of the cells with the first level occurs in the first group.

5. The cell transfer apparatus according to claim 1, wherein
    the cell transfer head includes a plurality of tips that can suck and discharge the cells, in a predetermined arrangement state, the plurality of tips being configured to suck the cells in the holders and discharge the cells to the plurality of wells, and
    the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

6. A cell transfer method for transferring a cell held in a dish to a microplate where a plurality of wells are classified into a plurality of groups, the cell transfer method comprising:

capturing an image of the dish in which the cell to be transferred is held;

giving evaluation levels to the plurality of the cells held in the dish, respectively, based on the image of the dish with reference to predetermined multiple-step evaluation levels for the cells;

setting transfer destinations of the plurality of the cells on the dish so that the cells equal in evaluation level are distributed evenly to each of the plurality of groups in the microplate; and transferring the plurality of the cells held in the dish to the plurality of wells in the plurality of groups in the microplate, respectively, based on the setting of the transfer destinations.

7. The cell transfer apparatus according to claim 2, wherein a culture solution is poured into the plurality of wells of the microplate, and the plurality of groups are classified based on a condition of the culture solution.

8. The cell transfer apparatus according to claim 2, wherein in a case where the evaluation levels include a first level and a second level lower in grade than the first level, and the plurality of groups include n groups, the allocation processor is configured to allocate, to each of the plurality of groups a/n pieces of transfer destination addresses and b/n pieces of transfer destination addresses when "a" pieces of the cells with the first level exist and "b" pieces of the cells with the second level exist, and when "a" is indivisible by "n", the allocation processor is configured to set a first group to which the cells with the first level are distributed, a number of the cells being a quotient of a/n, and a second group to which the cells are distributed, a number of the cells being obtained by adding each of remainders of a/n to the quotient, and allocate the cells with the second level preferentially to transfer destination addresses where a shortfall of the cells with the first level occurs in the first group.

9. The cell transfer apparatus according to claim 3, wherein in a case where the evaluation levels include a first level and a second level lower in grade than the first level, and the plurality of groups include n groups, the allocation processor is configured to allocate, to each of the plurality of groups a/n pieces of transfer destination addresses and b/n pieces of transfer destination addresses when "a" pieces of the cells with the first level exist and "b" pieces of the cells with the second level exist, and when "a" is indivisible by "n", the allocation processor is configured to set a first group to which the cells with the first level are distributed, a number of the cells being a quotient of a/n, and a second group to which the cells are distributed, a number of the cells being obtained by adding each of remainders of a/n to the quotient, and allocate the cells with the second level preferentially to transfer destination addresses where a shortfall of the cells with the first level occurs in the first group.

10. The cell transfer apparatus according to claim 7, wherein in a case where the evaluation levels include a first level and a second level lower in grade than the first level, and the plurality of groups include n groups, the allocation processor is configured to allocate, to each of the plurality of groups a/n pieces of transfer destination addresses and b/n pieces of transfer destination addresses when "a" pieces of the cells with the first level exist and "b" pieces of the cells with the second level exist, and when "a" is indivisible by "n", the allocation processor is configured to set a first group to which the cells with the first level are distributed, a number of the cells being a quotient of a/n, and a second group to which the cells are distributed, a number of the cells being obtained by adding each of remainders of a/n to the quotient, and allocate the cells with the second level preferentially to transfer destination addresses where a shortfall of the cells with the first level occurs in the first group.

11. The cell transfer apparatus according to claim 2, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

12. The cell transfer apparatus according to claim 3, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

13. The cell transfer apparatus according to claim 4, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

14. The cell transfer apparatus according to claim 7, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

15. The cell transfer apparatus according to claim 8, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

16. The cell transfer apparatus according to claim 9, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

17. The cell transfer apparatus according to claim 10, wherein the cell transfer head includes a plurality of tips that can suck and discharge the cells, in a predetermined arrangement state, the plurality of tips being configured to suck the cells in the holders and discharge the cells to the plurality of wells, and the allocation processor is configured to reset, within a setting range, transfer destinations of the cells so that the cells can be discharged simultaneously from the plurality of tips to the plurality of wells, the setting range being a setting range where the cells equal in evaluation level are distributed evenly to each of the plurality of groups.

\* \* \* \* \*